(12) United States Patent
Fischell et al.

(10) Patent No.: US 6,985,771 B2
(45) Date of Patent: Jan. 10, 2006

(54) RAPID RESPONSE SYSTEM FOR THE DETECTION AND TREATMENT OF CARDIAC EVENTS

(75) Inventors: Robert E. Fischell, Dayton, MD (US); David R. Fischell, Fair Haven, NJ (US); Tim A. Fischell, Richland, MI (US)

(73) Assignee: Angel Medical Systems, Inc., Tinton Falls, NJ (US)

( * ) Notice: Subject to any disclaimer, the term of this patent is extended or adjusted under 35 U.S.C. 154(b) by 488 days.

(21) Appl. No.: 10/051,743

(22) Filed: Jan. 22, 2002

(65) Prior Publication Data

US 2003/0139778 A1    Jul. 24, 2003

(51) Int. Cl.
    A61B 5/04    (2006.01)
(52) U.S. Cl. .......................................... 607/3
(58) Field of Classification Search ................ 607/1–9; 604/288.01, 288.02
    See application file for complete search history.

(56) References Cited

U.S. PATENT DOCUMENTS

| | | | |
|---|---|---|---|
| 3,724,455 A * | 4/1973 | Unger | 600/515 |
| 4,657,536 A | 4/1987 | Dorman | |
| 4,784,646 A | 11/1988 | Feingold | |
| 5,009,644 A * | 4/1991 | McDonald | 604/175 |
| 5,113,869 A | 5/1992 | Nappholz et al. | |
| 5,135,004 A | 8/1992 | Adams et al. | |
| 5,313,953 A | 5/1994 | Yomtov et al. | |
| 5,497,780 A | 3/1996 | Zehender | |
| 5,827,204 A * | 10/1998 | Grandia et al. | 601/2 |
| 6,083,248 A * | 7/2000 | Thompson | 607/30 |
| 6,112,116 A | 8/2000 | Fischell et al. | |
| 6,272,379 B1 | 8/2001 | Fischell et al. | |
| 6,501,983 B1 | 12/2002 | Natarajan et al. | |
| 6,514,195 B1 * | 2/2003 | Ferek-Petric | 600/17 |
| 6,577,899 B2 * | 6/2003 | Lebel et al. | 607/60 |
| 6,656,125 B2 * | 12/2003 | Misczynski et al. | 600/508 |
| 2003/0139785 A1 * | 7/2003 | Riff et al. | 607/60 |

* cited by examiner

Primary Examiner—Scott M. Getzow

(57) ABSTRACT

Disclosed is a system for detecting an acute myocardial infarction (i.e., a heart attack) at the earliest possible time and promptly warning the patient that he should immediately seek medical care. The present invention includes an implantable electronic system that can sense a change in the patient's electrogram that is indicative of a heart attack. If a heart attack is sensed, the device would then cause an implantable and/or externally located alarm to be actuated to warn the patient of his condition and a medical practitioner at a remote diagnostic center would receive the patient's electrogram for analysis. The patient or a caretaker would then be informed to self-inject medication through a subcutaneous, pass-through drug port that can be a separate device or integrated into the implanted device that is designed for the early detection of a heart attack. Since an implantable heart pacemaker or defibrillator already has within its structure many of the elements required for the device to recognize a heart attack, it would be expeditious to add a capability to these existing devices to detect a heart attack, have a pass-through drug port and provide an implantable and/or external alarm means to inform the patient to take appropriate action.

88 Claims, 13 Drawing Sheets

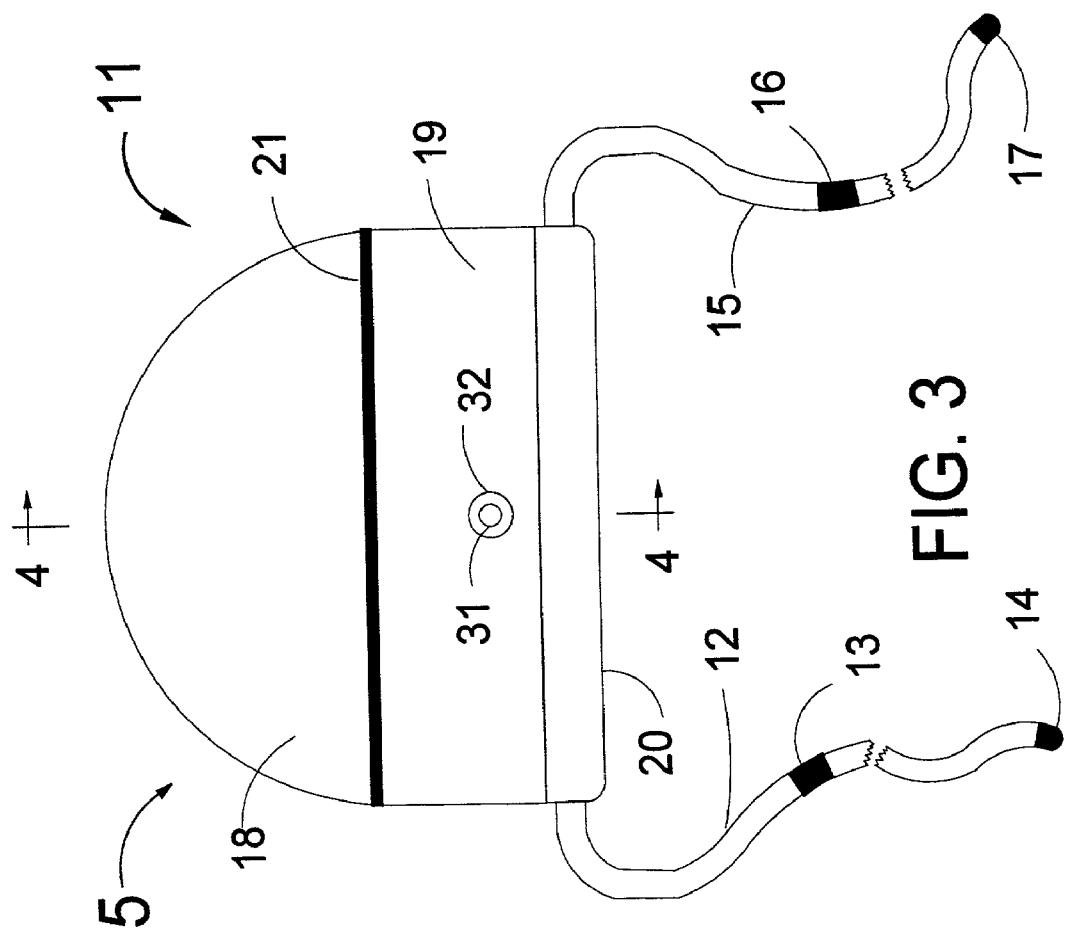

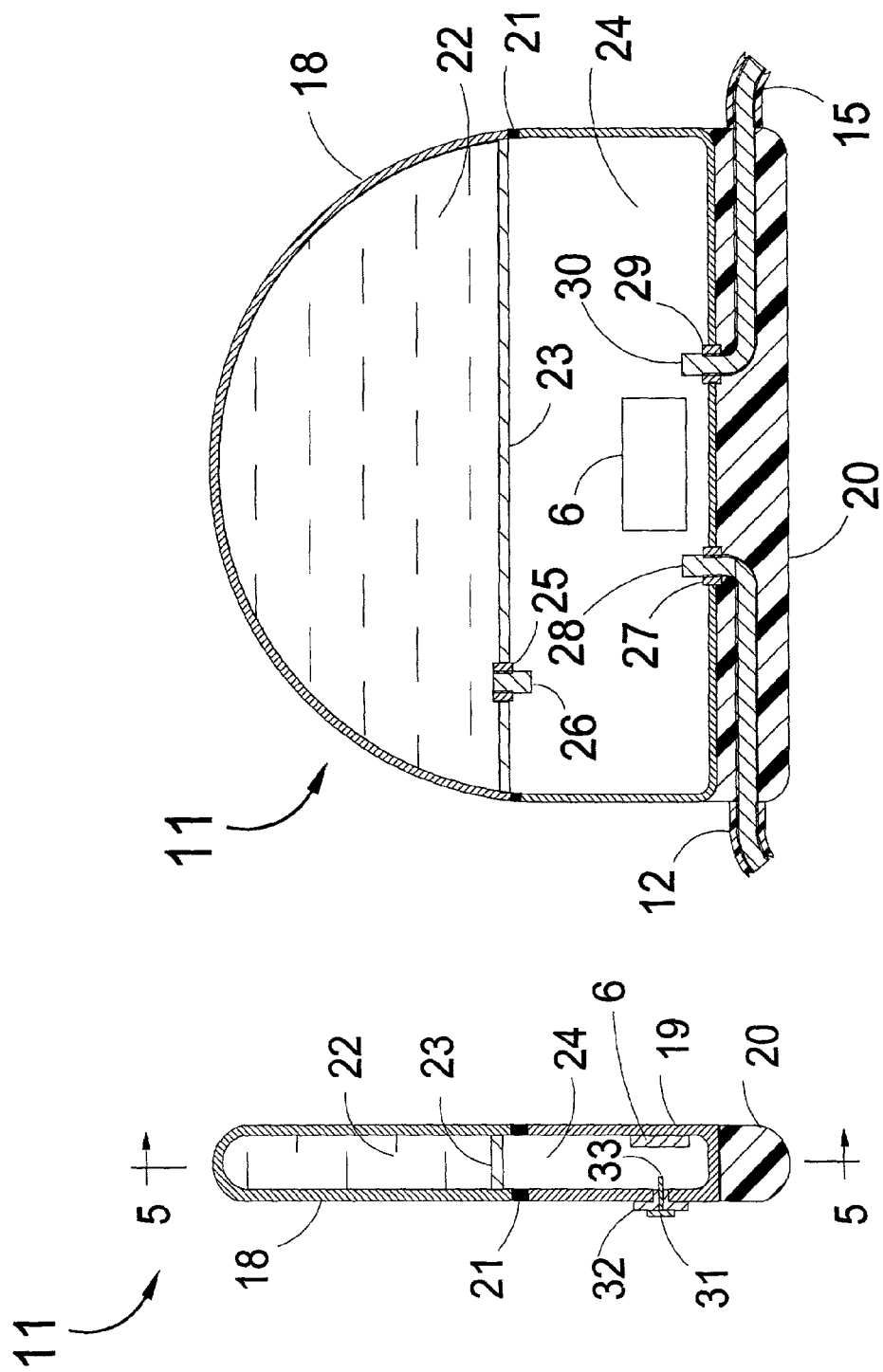

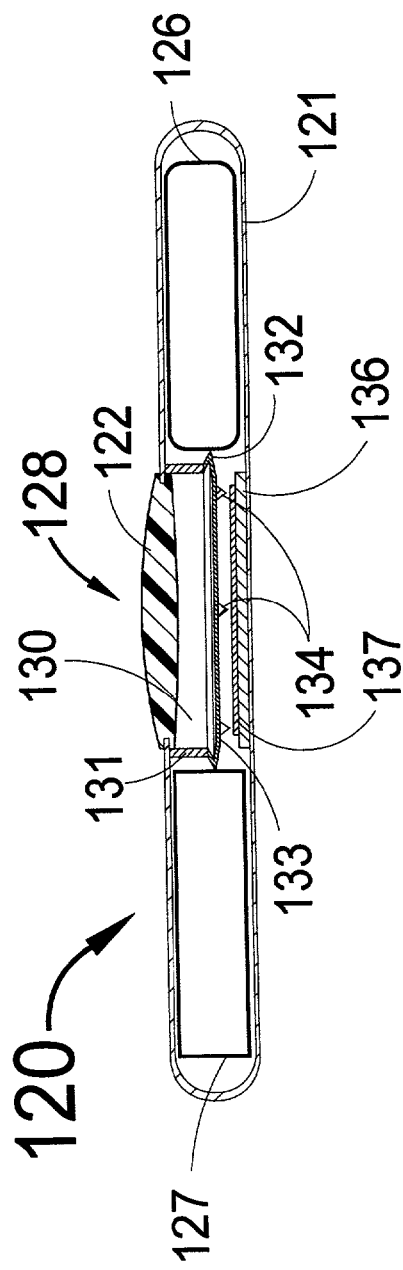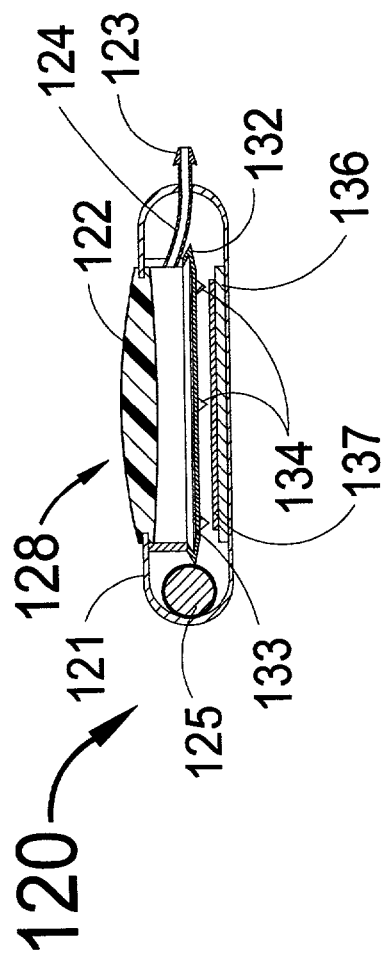

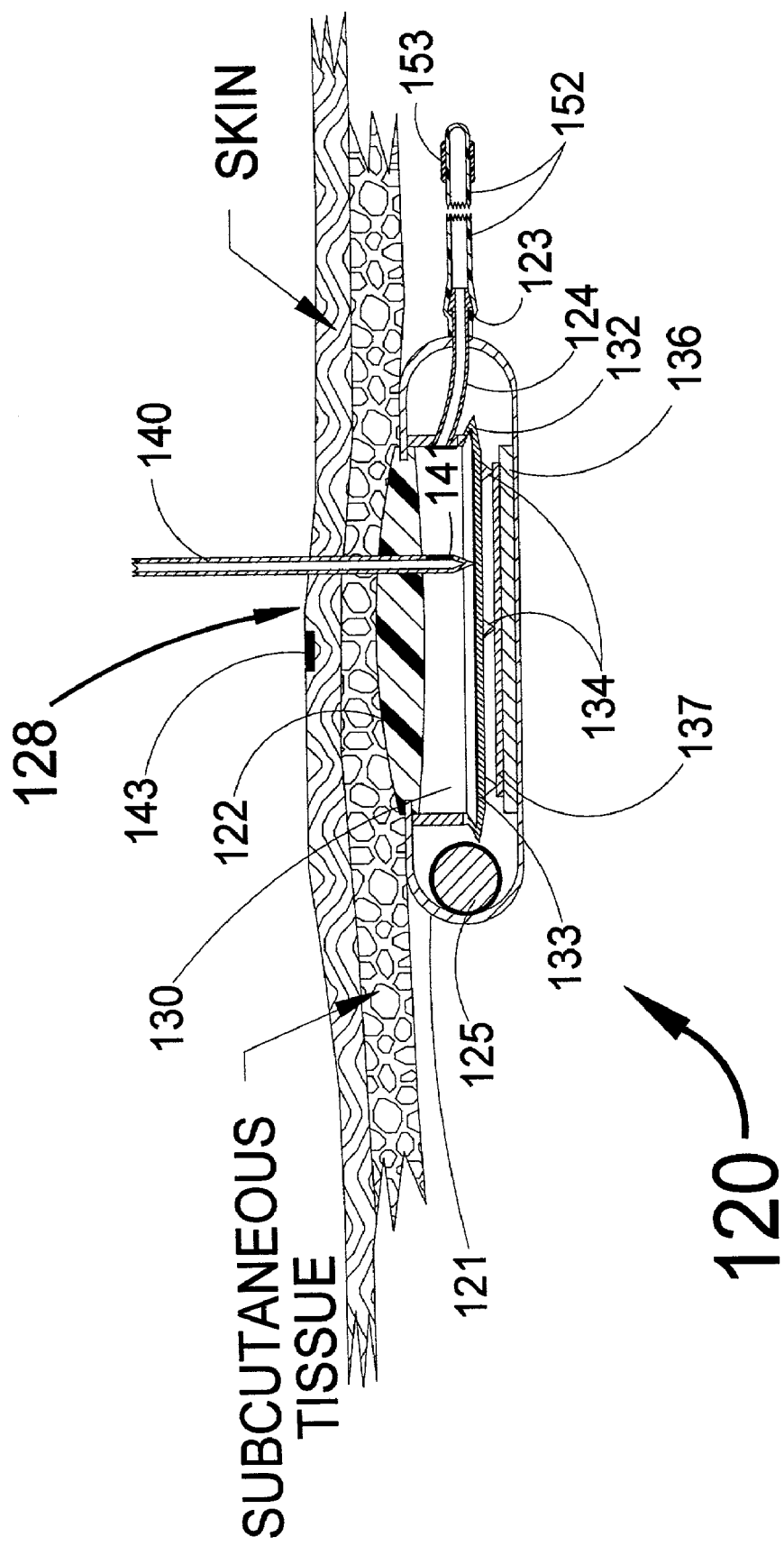

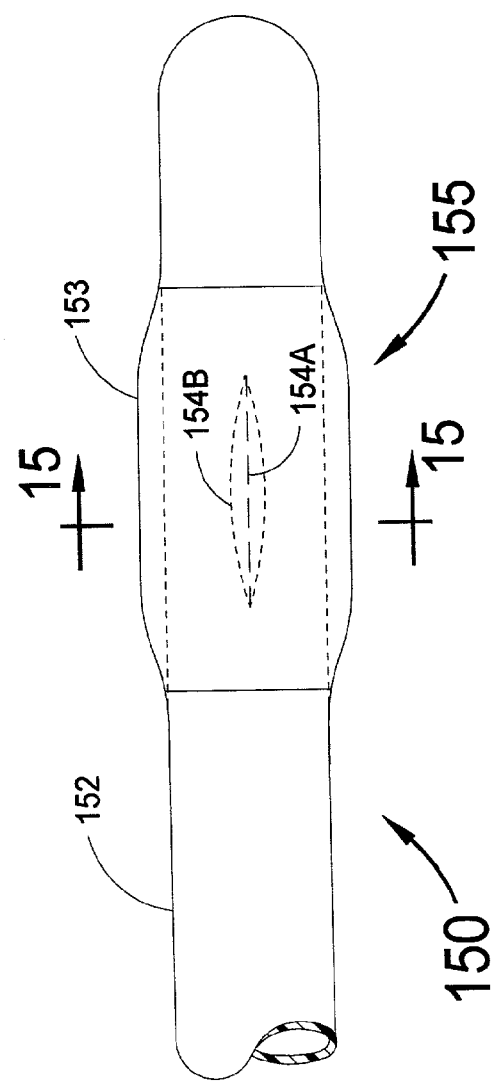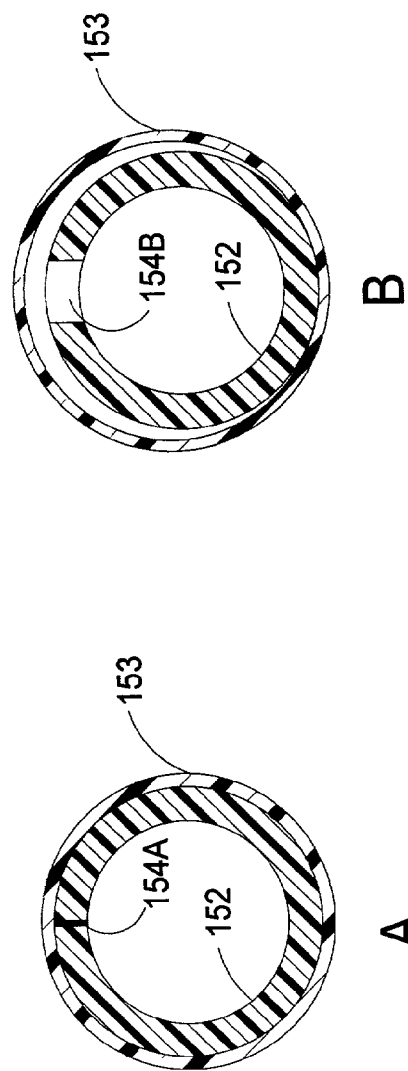
FIG. 14
FIG. 15

RAPID RESPONSE SYSTEM FOR THE DETECTION AND TREATMENT OF CARDIAC EVENTS

FIELD OF USE

This invention is in the field of systems, including devices implanted within a human patient, for the purpose of automatically detecting the onset of a cardiac event and promptly providing appropriate medical care to prevent death and/or damage to the heart muscle.

BACKGROUND OF THE INVENTION

Heart disease is the leading cause of death in the United States. A common and life-threatening complication of heart disease is myocardial infarction resulting from a thrombus that obstructs blood flow in one or more coronary arteries. The sooner thrombolytic medication such as tissue plasminogen activator (tPA) or urokinase is placed into the patient's bloodstream after the occurrence of an acute myocardial infarction, the sooner an obstructive thrombus will be dissolved and perfusion of the myocardium will be restored. The extent of damage to the myocardium is strongly dependent on the length of time that occurs prior to restoration of some blood flow to the heart muscle. At this time, no system exists that provides for early and automatic detection of an acute myocardial infarction and for rapidly providing the patient with a prescribed dose of a thrombolytic medication.

There are many patients who have implanted heart pacemakers or implanted cardiac defibrillators (ICDs). The purpose of the pacemaker is to provide a low energy electrical stimulation pulse that causes the heart to beat at a prescribed rate. The purpose of the defibrillator is to shock the heart back into sinus rhythm after ventricular fibrillation has been detected. However, no existing implantable pacemaker or defibrillator is also able to detect a partial or complete blockage of a coronary artery and warn the patient that this potentially fatal event is occurring. Furthermore, no pacemaker or ICD is presently used with an external communication and action system that rapidly responds to acute myocardial infarction or reversible myocardial ischemia that is detected by specially designed circuitry in that implanted pacemaker or ICD.

Although anti-tachycardia pacemakers and ICDs can detect heart arrhythmias and respond with electrical stimulation, none are currently designed to be part of a rapid response system designed to inform the patient as to his condition and to facilitate the injection of an anti-arrhythmic drug with a minimum time delay.

It is well known that an acute myocardial infarction can be detected from a patient's ECG by noting an ST segment deviation (i.e., voltage change) as compared to the voltage of the patient's TP or PQ segments. Such an ST segment deviation can be even more clearly discerned with electrodes implanted within the body (especially within or in close proximity to the heart) as compared with detecting the elevated ST segment from chest and/or limb mounted electrodes.

In U.S. Pat. Nos. 6,112,116 and 6,272,379 issued to R. E. Fischell, et al, an implanted cardiosaver system is described that includes an automatic delivery of medication when a heart attack is detected. These patents also teach the combination of internal and external alarm systems for informing the patient that a heart attack has been detected. However, the long term storage of any thrombolytic or anti-thrombogenic medication within a human patient can cause a deterioration of such drugs. Except for the treatment of an acute myocardial infarction, neither of these patents teaches how an external system could be used to treat any potentially fatal or at least worrisome cardiac event such as an arrhythmia and/or myocardial ischemia that is caused by an elevated heart rate resulting from physical effort including exercise.

In U.S. Pat. No. 5,479,780 by M. Zehender, a device is described that has a "goal of eliminating . . . cardiac rhythm abnormality." In order to accomplish this goal, Zehender requires exactly two electrodes placed within the heart and exactly one electrode placed outside the heart. Although multiple electrodes could be used, an ideal sensor for providing an electrogram to detect a heart attack would use a single electrode placed within the heart. The Zehender patent teaches the detection of an ST segment deviation to indicate coronary ischemia and to use an implanted drug pump to release medication to treat such an ischemia. However, Zehender never discusses the treatment of acute myocardial infarction. Rather, the purpose of Zehender's invention is only to warn of an arrhythmia caused by myocardial ischemia. Zehender does not indicate that his invention could be used for the treatment of a heart attack. Furthermore, Zehender does not consider the problem of drug deterioration when such a drug is stored within an implanted device for later release when ischemia is detected. Still further, ischemia can result from exercise when there is progression of a stenosis in a coronary artery. Under such circumstances it would be highly undesirable to release a medication designed to treat the ischemia caused by a heart attack. Furthermore, Zehender does not describe an external system to be used in conjunction with an implanted cardiosaver device. Thus Zehender does not teach the use of an external alarm means or means to have a diagnostic center always on call for immediate diagnosis of a potentially fatal heart attack or arrhythmia. Furthermore, Zehender does not teach an implanted drug port that can be used for rapidly providing a bolus of medication from an external source to be delivered into a patient having a heart attack by either the patient himself, a caretaker of the patient or by a paramedic from an ambulance. Although Zehender does describe the use of a pacemaker or defibrillator in conjunction with an implanted device for detecting ischemia, he does not describe either an external alarm system to be used with the implant, nor does he describe the use of an implanted drug port to be used with the pacemaker or defibrillator.

The electrical signal from the heart as measured from electrodes within the body is called an a "electrogram". The early detection of an acute myocardial infarction or myocardial ischemia caused by an increased heart rate or exertion is clearly feasible by using an implantable system that notes a change in a patient's electrogram. The implanted device portion of such a system is defined herein as a "cardiosaver" and the entire system including the implanted cardiosaver and the external portions of the system is defined herein as the "cardiosaver system." Furthermore, although the masculine pronouns "he" and "his" are used herein, it should be understood that the patient or the medical practitioner who treats the patient could be a man or a woman. Still further the term; "medical practitioner" shall be used herein to mean any person who might be involved in the medical treatment of a patient. Such a medical practitioner would include, but is not limited to, a medical doctor (e.g., a general practice physician, an internist or a cardiologist), a medical technician, a paramedic, a nurse or an electrogram analyst. A "caretaker" is defined herein as a person that can come to the aid of the patient if the cardiosaver system indicates the occurrence of some cardiac related event such as a heart attack or ventricular fibrillation. A caretaker would include, but is not limited to, the patient's spouse, an attendant in a nursing home, a nurse or any person assigned to help take care of the patient. A "cardiac event" includes an acute myocardial infarction, ischemia caused by effort (such as exercise) and/or an elevated heart rate, bradycardia, tachycardia or an arrhythmia such as atrial fibrillation, atrial flutter, ventricular fibrillation, and premature ventricular or atrial contractions (PVCs or PACs). The use of this invention to treat stroke, will for the purposes of this specification, also be considered to be a "cardiac event". For the purpose of this invention, the term "electrogram" is defined to be the signal from an implanted electrode that is placed in a position to indicate the heart's electrical activity.

SUMMARY OF THE INVENTION

One embodiment of the present invention is an implanted medical device that is an implanted cardiosaver, that can detect the occurrence of an acute myocardial infarction (AMI), i.e., a heart attack, within less than five minutes after it occurs and then automatically alarm the patient that this event is occurring. The patient's warning can come from an alarm means implanted in the patient's body and/or from an externally located alarm means that receives a wireless signal from the cardiosaver.

The cardiosaver system is designed to minimize damage to the patient's heart from an acute myocardial infarction (i.e., a heart attack) by detecting the AMI at the earliest possible time and promptly warning the patient that he should immediately seek medical care. To do this, in addition to the implanted cardiosaver, the cardiosaver system includes an external alarm system located external to the patient. The external alarm system provides an external alarm capable of waking the patient if he is sleeping in addition to the internal alarm built into the implanted cardiosaver. The external alarm system also has the capability to transmit the cardiac event alarm and recorded electrogram data collected by the implanted cardiosaver to a medical practitioner at a remotely located diagnostic center. It is also envisioned that the external alarm system could also transmit patient information such as an identifying number, name, medical history and patient location in addition to the electrogram. The external alarm system may be either a fixed location alarm system located at the patient's normal residence or a portable alarm system that can be carried by the patient. The external alarm system is also capable of transmitting the patient's electrogram both prior to and in real time during the cardiac event to the medical practitioner.

A network operation support system at a network operation center is another important portion of the external equipment for the cardiosaver system. The network operation support system receives cardiac event alarms from the external alarm system, identifies the patient, finds the next available medical practitioner at the cardiosaver diagnostic center and provides a display of the patient's medical record and electrogram data from the implanted cardiosaver for consideration by the medical practitioner. Along with the patient medical history, the patient medical record includes the prescription for treatment of specific cardiac events, which prescription is written by the patient's own physician. The network operation support system also provides to the medical practitioner at the diagnostic center, the phone number for the emergency medical services (EMS) facility that is closest to the patient's location and also directions to the patient's location. If the alarm is received from the fixed location alarm system, the emergency medical services phone number and directions are in the medical record. If the portable alarm system is used, the network operation support system will look up in its own internal database the phone number for the emergency medical services closest to the location of the patient. By "closest" is meant the EMS that can arrive at the patient's location in the shortest possible time. This shortest time determination could also include considerations relative to traffic conditions at the time that the emergency call is made.

The portable alarm system which will work through existing cell phone wireless networks will provide a location either by triangulation from the cell phone system or through a built in GPS locator capability. The network operation support system would typically be a software package run on one or more computers located in one or more network operation center. The diagnostic center(s) will have one or more medical practitioners either located at the diagnostic center or networked in from remote sites. It is envisioned that the diagnostic center medical practitioner would also have the capability to communicate by phone and/or data communication (instant messaging e-mail) to the patient and/or his personal physician to implement the most rapid treatment for the patient.

To assure privacy of the patient's name, condition and medical history, the cardiosaver system can also include a security system capability. This security system can include identifying the patient only by a patient identification number that is programmed into the implanted cardiosaver, by using computer systems whose function is to operate the cardiosaver system while maintaining the patient's privacy using means and by other methods that are well known in the art to provide security for patient's names and medical records. Furthermore, it is envisioned that the patient would select a single name (typically a first name or a nickname) that would be used by the medical practitioner at the diagnostic center to address the patient over a telephone line. This single name could correspond to a unique patient identifying number. Use of current virtual private network (VPN) systems and services can also facilitate the security of the entire cardiosaver system by linking all the elements (external alarm system, network operation support system, physician's terminal for data record management and the diagnostic center) in a secure manner. The network operation support system database would contain patient medical records that are periodically updated by the patient's physician from a secure terminal typically located at the primary office of the patient's physician.

The implanted cardiosaver can sense a change in the patient's electrogram that is indicative of an acute myocardial infarction. If an acute myocardial infarction is sensed, the cardiosaver would then cause an implantable and/or externally located alarm means such as an audio sound source or a subcutaneous electrical tickle to be actuated in order to warn the patient of his condition. The patient could then promptly seek medical care, for example, at a hospital emergency room. Having been trained to recognize such an alarm, most patients would neither fail to recognize such an indication of a cardiac event nor would they ignore such an alarm signal if it were to occur.

Since an implantable heart pacemaker or defibrillator already has within its structure and electronic circuitry many of the elements required to function as a cardiosaver, it would be expeditious to add cardiosaver system capability to these existing devices to detect an acute myocardial infarction and provide implantable and external alarm means to inform the patient to take appropriate action. Specifically, most implantable pacemakers or defibrillators already have a long-lived battery, one or more electrodes connected by a lead wire to an electrogram amplifier within a hermetically sealed metal case and electrogram storage capability. These same elements can be part of an implanted system that can be used to detect an acute myocardial infarction and alarm the patient accordingly. The pacemaker or defibrillator that includes a capability for early detection of an acute myocardial infarction can be used to cause the external alarm system to transmit electrogram and other patient data to the diagnostic center medical practitioner who can summon the emergency medical services to promptly get to the patient and apply pre-prescribed thrombolytic and/or anti-thrombogenic medication(s).

The implanted alarm located within the cardiosaver can be either an acoustic alarm, a mechanical vibration or a subcutaneous electrical tickle. Any one of these implanted signals could be applied periodically, for example, with a 5 second on-time every 30 seconds after the detection of a heart attack. It is envisioned to turn the internal alarm off after a reasonable time period that is probably less than 30 minutes. The external alarm would be accomplished by means of a wireless (typically wireless) receiving system that causes an audio alarm to occur when a wireless signal is received from the implanted cardiosaver. The external audio alarm from the cardiosaver external alarm system can inform the patient that heart attack has been detected by his implanted system. It could also inform him (e.g., by a pre-recorded human voice) that he should promptly take some predetermined medication such as chewing two aspirins and/or injecting thrombolytic drugs into the implanted drug port in the cardiosaver, and that he should wait for the arrival of emergency medical services or he should promptly proceed to an emergency medical facility.

When the alarm signal arrives at the diagnostic center, the medical practitioner will review the electrogram data from the patient's cardiosaver. If the medical practitioner recognizes that the patient is having an acute myocardial infarction, the medical practitioner can inform the emergency medical services crew on an ambulance to deliver to the patient a dosage of a thrombolytic and/or anti-thrombogenic medication(s) to minimize damage to the patient's heart tissue. If ischemia during exercise is recognized, the medical practitioner at the diagnostic center would ask the patient to stop exercising so that the alarm would go away. He would then inform the patient that he should see his own physician to determine what caused the ischemia during exercise. The external alarm system could also have a patient operated initiator that could be used to send electrogram data both from memory storage and in real time to a medical practitioner at the diagnostic center. This might be done in the event of any arrhythmia including, but not limited to premature atrial or ventricular beats, atrial fibrillation, atrial flutter or any other heart rhythm irregularities. The diagnostic center medical practitioner could then advise the patient what action, if any, should be taken. The cardiosaver system could also be programmed to send an alarm in the case of ventricular fibrillation so that a caretaker of the patient could be informed to immediately provide a defibrillation electrical stimulus. This is procedure is practical as home defibrillation units are now commercially available.

It is very important to note that the exact type and quantity of medication that the emergency medical services paramedics will deliver into the patient at the direction of the diagnostic center medical practitioner will have been previously determined by the patient's own physician and not (typically) by the diagnostic center medical practitioner. This is due to the fact that the patient's own physician is most familiar with the patient's weight, adverse reaction to some specific medication and other factors that make the patient's physician the ideal person to determine in advance what treatment his patient should receive if the patient has a heart attack or some other cardiac event. The role of the diagnostic center medical practitioner is merely to recognize from the electrogram that a cardiac event has occurred and to authorize the patient, the patient's caretaker or the emergency medical services paramedics to administer the pre-prescribed drug regimen determined in advance by the patient's physician. If for some reason the patient's physician has not been given advance instructions, then the diagnostic center medical practitioner would be able to prescribe an appropriate drug regimen for that patient.

The emergency medical services crew (or the patient himself or the patient's caretaker) can also use an external device to provide a vibratory input in the region of the patient's heart after medication is injected in order to assist in breaking up the newly formed blood clot. It is also anticipated that the implanted cardiosaver could include means for having a mechanical vibration impressed from inside the heart to enhance the break up of an artery blocking thrombus. The emergency medical services paramedics could also provide a defibrillation shock if the patient is experiencing ventricular fibrillation.

It is believed that the cardiosaver system described herein is extremely valuable because many patients who have early symptoms of an acute myocardial infarction such as indigestion or left arm pain or even a chest discomfort very often tend to ignore these warning signs. If, for example, the patient experiences some indigestion that has an associated elevated ST segment that is indicative of an acute myocardial infarction, then promptly notifying the patient of this condition can significantly decrease the mortality and morbidity associated with acute myocardial infarction. Furthermore, approximately 20% of all patients who have an acute myocardial infarction have a "silent MI" with no detectable symptoms whatsoever. This is very often the case for elderly individuals, particularly if they have had diabetes for many years. The invention described herein would be of particular value for such patients.

The fact that no alarm will result from symptoms that mimic an acute myocardial infarction will provide reassurance to the patients when such false heart attack indications occur. What is most important is that, whenever a major heart attack occurs that compromises a large section of the myocardium, there is generally a significant ST segment shift that should be clearly discernible by the implanted cardiosaver. If a small area of the heart muscle is involved, it is possible that the ST segment deviation will not be readily detected. However, a smaller infarction would result in a much less serious outcome for the patient.

Another embodiment of the cardiosaver system involves the administration (i.e., injection) of a thrombolytic, anti-platelet and/or anti-thrombogenic medication directly into the patient's blood circulation by means of a pass-through drug port that can be separately implanted or formed into (i.e., integrated into) the implanted cardiosaver. Such a port would typically employ a septum on its outer surface whose location just under the patient's skin is easily detectable by its shape, location and also by a tattoo mark on the skin. Such a tattoo mark would be placed on the skin directly over the center of the port's septum. Either or both the patient or his caretaker would be trained to inject an appropriate medication that has been pre-prescribed by his physician through the patient's skin and through the septum located on the cardiosaver. The cardiosaver has a catheter in fluid communication with its drug port to deliver a bolus of the injected medication rapidly and directly into the patient's bloodstream. One way to deliver the drug would be by means of a separate drug delivery catheter that is in fluid communication with the cardiosaver's drug port. Alternatively, a drug delivery lumen in the electrical lead that is used to sense the patient's electrogram could be used to deliver the medication. In either case, the catheter or lead with a drug delivery lumen (either of which is defined herein as the "medication delivery catheter") would be placed so that its proximal end is joined to the cardiosaver device and its distal end would lie in the patient's bloodstream, typically in a vein, the superior vena cava or inside the heart itself. Such placement is well known to those medical practitioners who implant the electrical leads for pacemakers of defibrillators. A valve located at or near the distal end of the medication delivery catheter would prevent blood from entering the medication deliver catheter. This valve would automatically open when medication is injected by a hypodermic syringe through the septum, through the drug chamber in the cardiosaver and finally through the medication delivery catheter.

As a safety means to indicate that the distal end of the needle of the hypodermic syringe is properly situated at the bottom of the drug chamber of the drug port, a unique audio signal is emitted from the cardiosaver when the needle is properly placed. For example, if the indication of a heart attack is a 5 second sound burst every 30 seconds, then the indication of proper placement of the needle point within the drug chamber of the drug port could be a sound that is continuous as long as the distal end of the needle is pushing on the bottom surface of the drug chamber. Such a sound would assure the patient or the caretaker that the plunger on the hypodermic syringe could be pushed forward to rapidly deliver a bolus of the drug into the patient's bloodstream. The rapid delivery of a bolus of the drug would be clearly advantageous for dissolving a thrombus as compared to the comparatively slow drug release that could be accomplished by an implanted drug pump.

It is envisioned that the drug port would contains a liquid solution that has the same osmolality as blood. The liquid solution would also contain an anti-bacterial ingredient to prevent the build up of any bacteria within the drug port or the medication delivery catheter. The liquid solution would not typically contain any thrombolytic or anti-thrombogenic medication. A normal saline solution that includes any anti-bacterial substance commonly used as a preservative for liquid medications could be used for this purpose. This liquid solution would be replaced into the drug port after any injection of a treatment medication has been accomplished. Furthermore, the patient or his caretaker might usefully practice the injection of this solution on a periodic basis, such as once a year, in order to maintain their competency for injecting medication on an emergency basis. It will be of particular value for the patient or his caretaker to hear the sound that the implanted cardiosaver device produces when the needle of the hypodermic syringe is properly placed so that the plunger can be pushed to rapidly deliver a bolus of the drug into and through the drug port and into the patient's bloodstream. The periodic injection of the liquid solution must, of course, not cause any harm to the patient.

It is also envisioned that the drug port and cardiosaver capability could be incorporated into a pacemaker or a defibrillator. Thus, all the features described herein for a cardiosaver device, could be included into an implanted device that includes pacing and/or defibrillation capabilities. Furthermore, a pacemaker or defibrillator with cardiosaver capabilities could be used with a separate drug port and with all the external equipment that is described herein.

It should also be understood that a cardiosaver device with a drug port would be very advantageous for medication delivery in an ambulance or at a hospital or similar medical facility. Having a drug port that provides the most rapid access to the patient's bloodstream can save valuable time as compared to the time required to place an intravenous catheter into a patient's vein. This time saving is particularly important for the patient and it would make the application of an intravenous injection much easier for the paramedics who usually are the first to get to such a patient. It should also be understood that the drug port could be used for the injection of other systemically administered medications such as beta-blockers, anti-arrhythmic drugs, etc.

The type(s) of drugs that would be available for such delivery through a drug port are generally thrombolytic agents, anti-thrombogenic agents, anti-arrhythmic agents or a blend of more than one medication. A typical thrombolytic agent could be tPA, urokinase, streptokinase or any similar agent designed to dissolve a thrombus. A typical anti-thrombogenic medication could be ReoPro, heparin, Plavix or any similar medication. It is important to note that the method to decrease morbidity and mortality from an acute myocardial infarction would include having the patient's own physician write a prescription for the exact type(s) and quantity of medication(s) that he would want the patient to have if a heart attack or other cardiac event would occur. The type(s) and amount would depend on what is available at any time as the best single drug or drug combination. Another consideration would be any known reaction of the patient to a particular medication. The amount of drug that is prescribed might also depend on the patient's sex and weight. For example, a 250-pound man would probably use a larger dose or different type of medication as compared to a 100-pound woman. The cardiosaver system also envisions the delivery of an anti-arrythmic drug for specific types of arrhythmias and other potentially beneficial drugs such as beta-blockers, nitrates, etc. that can improve the outcome for patients who have a myocardial infarction.

It is well known that patients who have just had a heart attack become very fearful of a later heart attack that can be fatal or can result in significant damage to the heart muscle. An important advantage of the cardiosaver system (including its use within a pacemaker or defibrillator) as taught herein is that it can be used to assure the patient that future heart attacks will be detected and treated so rapidly that his chance of surviving without significant heart damage is very high. Therefore, a placebo effect for this device is expected to decrease the morbidity and mortality of these patients as compared to patients who do not have an implanted cardiosaver device and are not enrolled into the cardiosaver system.

Another important concept for this invention is a method for determining the type of patient in whom the cardiosaver should be implanted. One such type of patient is a person who has diabetes as evidenced by a fasting blood sugar that is greater than 110 mg/dl. Therefore, the method to provide improved medical care for such a patient is to perform a blood test to determine if the fasting blood glucose is greater than 110 mg/dl, and if it is, then determine if the patient has at least one other predictor of an acute myocardial infarction. These predictors would include, but are not limited to, hypercholesterolemia, high blood pressure, proteinuria exceeding 250 mg in 24 hours, a prior heart attack or ischemic stroke, age greater than 65 or a family history of acute myocardial infarction. The inventive method that is taught herein includes the step of implanting a cardiosaver device into such a patient. The method could further include the step of making the patient part of the cardiosaver system so that lie could obtain rapid treatment for an acute myocardial infarction should it occur.

Another inventive method that is described herein includes a first step of implanting a stent into the patient's coronary artery. The next step in this method is to implant a cardiosaver into that patient and then to have the patient perform an exercise that is comparatively strenuous for that patient (e.g. a treadmill stress test). The next step is to program the cardiosaver cardiac event detection thresholds using the electrogram data recorded by the implanted cardiosaver as a baseline. The last step in this method would to advise the patient to seek medical care if during future exercise his implanted cardiosaver indicates that he had a deviation of the ST segment of his electrogram. It should be understood that the cardiosaver could provide a different alarm signal for ischemia caused by a heart attack as opposed to ischemia caused by exertion when the patient has a narrowed coronary artery. For example, for a heart attack, a 2–5 second on-time for an audio alarm could be programmed to occur every 10–15 seconds but for ischemia produced at the higher heart rates associated with exercise, when an ST segment deviation occurred because of a narrowed artery, the alarm could be a 1–2 second on-time every 30–60 seconds. Of course it should be understood that a larger variety of on-times and periods between alarm sounds could be used to signal for a variety of different electrogram signals that could be analyzed by the cardiosaver. At least two of these are different alarm signals could provide a differentiation between ischemia during exercise as opposed to the occurrence of heart muscle injury resulting from an acute myocardial infarction. In any case, it is envisioned that the cardiosaver system provides the patient's electrogram to the medical practitioner at the diagnostic center in the event of any pre-programmed arrhythmia such as atrial fibrillation, atrial flutter, PVCs, PACs, etc.

An important aspect of this invention is that the patient's baseline electrogram would be measured after the cardiosaver has been implanted. The baseline electrogram would be measured at rest and during a treadmill stress test. These electrograms are made of record at least for review at the diagnostic center when a patient alarm occurs and also they could be programmed into the implanted cardiosaver device. In this way, the medical practitioner at the diagnostic center can compare the patient's baseline electrogram with the electrogram observed at the time when an alarm is indicated by the cardiosaver. By having the patient's baseline electrogram and his electrogram immediately before his heart attack and in real time during the heart attack, the diagnostic center medical practitioner is able to definitely determine the nature and extent of the heart problem being experienced by the patient.

Because patient's who are predisposed to a heart attack are also predisposed to a stroke, it is envisioned that an inventive method for treating stroke is accomplished by the use of the cardiosaver with a drug port as described herein. Specifically, if a patient has been taught the symptoms of a stroke, then the patient could use the cardiosaver system to inject thrombolytic and/or anti-thrombogenic medication through the drug port in his cardiosaver device under the advice and guidance of the medical practitioner at the diagnostic center. The patient's personal physician would arrange for any such arrangement in advance. Thus, the cardiosaver system could be used to significantly reduce the morbidity and mortality associated with stroke.

An important aspect of the cardiosaver system could be the use of a "panic button" on the external alarm system. When the panic button is pressed by the patient, it sends an alarm signal to the next available medical practitioner at the diagnostic center who would call the patient back to help identify the problem and if necessary summon appropriate assistance. The panic button could be used by the patient for any health event where the patient believes help is needed. Thus the cardiosaver system has application to many ailments other than AMI. In one embodiment of the present invention, the external alarm system is built into a wireless phone (either a cell phone or a cordless phone). In this case, the panic button actually initiates a voice call directly to the next available medical practitioner at the diagnostic center who would then talk to the patient to help identify the problem and summon the appropriate emergency medical services paramedics if necessary. For example if the patient were to have a stroke, either the patient or the patient's spouse, caretaker or partner could press the panic button, speak to a medical practitioner and be given instructions for injecting clot buster (thrombolytic) medication into the pass-through drug port of the cardiosaver.

Although the implanted cardiosaver could function without an external alarm system, the external alarm system is highly desirable. Thus, in its simplest form, the "cardiosaver system" includes the implanted cardiosaver, a physician's programmer and an external alarm system. The external alarm system can provide interpretation of the nature of the alarm if the detection of different cardiac events is programmed into the implanted cardiosaver. The external alarm system can also call out automatically to summon an emergency medical services ambulance at a number programmed into the external alarm system. The patient can also initiate electrogram recording through manual use of the external alarm system if he feels something is wrong. The recorded electrogram (from a detected cardiac event or manual patient initiation) could be read out by the physician's programmer at a later time. In this version, there would be no centralized monitoring service associated with the cardiosaver system. This version of the cardiosaver system might also include an implanted drug port as part of the cardiosaver. This would permit patient injection of thrombolytic agents or facilitate injection by the emergency medical services paramedics.

A more advanced embodiment of the cardiosaver system includes an implanted cardiosaver, an external alarm system and a network operation support system. The implanted cardiosaver would be capable of sensing a cardiac event and internally producing an alarm and store electrogram data. The external alarm system would be capable of sounding an audio alarm near the patient and calling out to a network operation support system. The network operation support system would be capable of presenting the patient's stored medical record along with the alarm data including the electrograms stored by the implanted cardiosaver and real time electrograms to a medical practitioner at a diagnostic center. The diagnostic center would act as the central monitoring station for incoming cardiac event alarms.

Thus it is an object of this invention is to automatically sense that a cardiac event has occurred by means of an implantable device called a "cardiosaver" which capability can also be provided in a pacemaker or defibrillator.

Another object of this invention to have a cardiosaver system including an implanted cardiosaver, an external alarm system and a network operation support system, the implanted cardiosaver being capable of sensing a cardiac event and internally producing an alarm, the external alarm system being capable of sounding an audio alarm near the patient and calling out to a network operation support system that includes patient medical records, the network operation support system being capable of presenting the patient's stored medical record along with the alarm data including real time and stored electrograms to a medical practitioner at a diagnostic center.

Still another object of this invention is to use the cardiosaver to warn the patient that an acute myocardial infarction has occurred by means of a subcutaneous electrical tickle or an audio signal.

Still another object of this invention is to have an implantable cardiac event detection device (a cardiosaver) that sends a wireless signal to an external alarm system that is located in close proximity to the patient. That external alarm system would inform the patient that he may be undergoing an acute myocardial infarction and that an emergency medical services ambulance has been called to bring him to a hospital and/or that he should take certain actions such as immediately going to an emergency room and/or promptly taking or injecting certain medications.

Still another object of this invention is to provide a means for informing the patient that he is having an acute myocardial infarction when he might otherwise ignore some particular symptom or he may not have had any detectable symptom.

Still another object of this invention is to provide a means to prevent a patient from believing that he is having a heart attack when in fact that is not happening.

Still another object of this invention is to provide a patient who has either an implanted heart pacemaker or defibrillator with the additional capability for sensing the occurrence of an acute myocardial infarction and promptly warning the patient that an acute myocardial infarction is occurring and further having an external alarm system that can result in the prompt arrival of an ambulance to treat the acute myocardial infarction.

Still another object of this invention is to provide a means and method for informing patients who have no symptoms associated with an acute myocardial infarction that they are having a heart attack and they should immediately seek medical assistance.

Still another object of this invention is to provide a patient with a cardiosaver system that can alarm the patient at all times for the purpose of obtaining medical assistance for that patient and for transmitting to a diagnostic center medical practitioner the patient's electrogram, medical history and location and further insulting in the arrival of an emergency medical services ambulance at the patient's home or any other location where the patient may be located, which ambulance includes paramedical personnel trained in the administration of drug therapy to treat a cardiac event (heart attack or arrhythmia) or a stroke.

Still another object of this invention is to provide the paramedics in an emergency medical services ambulance or the patient or the patient's caretaker with a device to provide vibration to the patient's heart to enhance the action of any medication delivered in the event of an acute myocardial infarction.

Still another object of this invention is to provide a patient with a portable external alarm system which includes an alarm means that can be with that patient at all times for the purpose of providing medical assistance for that patient and for transmitting to a diagnostic center medical practitioner the patient's electrogram and location and further resulting in the arrival of an emergency medical services ambulance at that patient's specific location.

Still another object of this invention is to have the portable external alarm system including a wireless phone capable of two-way voice communication.

Still another object of this invention is to have a panic button on the external alarm system of the cardiosaver system, the panic button allowing the patient to manually initiate an alarm to a central diagnostic center.

Still another object of this invention is to have the alarm initiated by the panic button be a "data alarm" similar to but distinctly different from the alarm generated by the detection of an acute myocardial infarction.

Still another object of this invention is to have the alarm initiated by the panic button be a voice telephone call that can be answered directly by personnel at a cardiosaver system diagnostic center.

Still another object of this invention is to provide a patient who has had an acute myocardial infarction with a cardiosaver system so as to reduce the probability that he has a later heart attack because of the placebo effect that the use of the cardiosaver system provides.

Still another object of this invention is to teach a method for reducing morbidity and mortality associated with a patient who has an increased probability for having a heart attack or stroke.

Still another object of this invention is to have a cardiosaver, including a cardiosaver capability within a pacemaker or defibrillator, which device includes a drug port that allows an externally located drug delivery device (such as a hypodermic syringe) to be used to inject medication into the patient's blood stream.

Still another object of this invention is to cause an audio signal to be emitted by the implanted cardiosaver device when the distal end of a needle of a hypodermic syringe is positioned within the drug port so that the plunger on the hypodermic syringe can be safely pressed to deliver a bolus of medication into and through the drug port and into the patient's bloodstream.

Still another object of this invention is to teach a method for having a patient determine if there is a further narrowing of a coronary artery by causing the cardiosaver device to sense a deviation of the ST segment of his electrogram as a function of increased heart rate, for example, during exercise.

Still another object of this invention is to have baseline electrograms of the patient both at rest and during exercise be accomplished; these data being made available to the reviewing medical practitioner at a diagnostic center and/or also stored as a baseline in the implanted cardiosaver device.

Still another object of this invention is to have different alarm signals when (1) an acute myocardial infarction is sensed as compared to the alarm signal that is provided when (2) there is an ST segment deviation caused by ischemia during exercise (or any other cause of tachycardia) or (3) the alarm signal is a result of an arrhythmia, or (4) the alarm is manually initiated by the patient by pressing a panic button.

Still another object of this invention is to have different alarm signals for different cardiac events detected by the implanted cardiosaver.

Still another object of this invention is have a faster detectable ST segment shift noted because the electrogram is sensed from within the heart as opposed to sensing the ECG from surface electrodes.

Still another object of this invention is to teach a method whereby the patient or a caretaker, upon recognizing the symptoms of a stroke, can use an implanted drug port to deliver medication to treat that stoke.

Still another object of this invention is to teach a method to apply a source of ultrasonic or other vibration in the vicinity of the heart for an acute myocardial infarction or in the vicinity of the brain for a stroke after a thrombolytic and/or anti-thrombogenic medication has been released into the patient.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 3 is a plan view of the cardiosaver showing the cardiosaver electronics module and two electrical leads each having two electrodes.

FIG. 4 is a cross section of the cardiosaver electronics module at section 4—4 of FIG. 3 showing separate sections for a battery, electronics and a header.

FIG. 5 is a cross section of the cardiosaver electronics module at section 5—5 of FIG. 4.

FIG. 11 is a cross section of the cardiosaver device at section 11—11 of FIG. 10.

FIG. 12 is a cross section of the cardiosaver device at section 12—12 of FIG. 10.

FIG. 13 is a highly enlarged cross section of a cardiosaver device showing details of the drug port with a fully inserted needle of a hypodermic syringe pushed against the bottom disk of a metal bellows of the drug port.

FIG. 14 is a top view of a distal portion of the medication delivery catheter.

FIG. 15 illustrates cross sections at section 15—15 of FIG. 14; the section at "A" showing the medication check valve in its closed position and the section at "B" showing the medication check valve is shown in its open position.

DETAILED DESCRIPTION OF THE INVENTION

Figure 1:
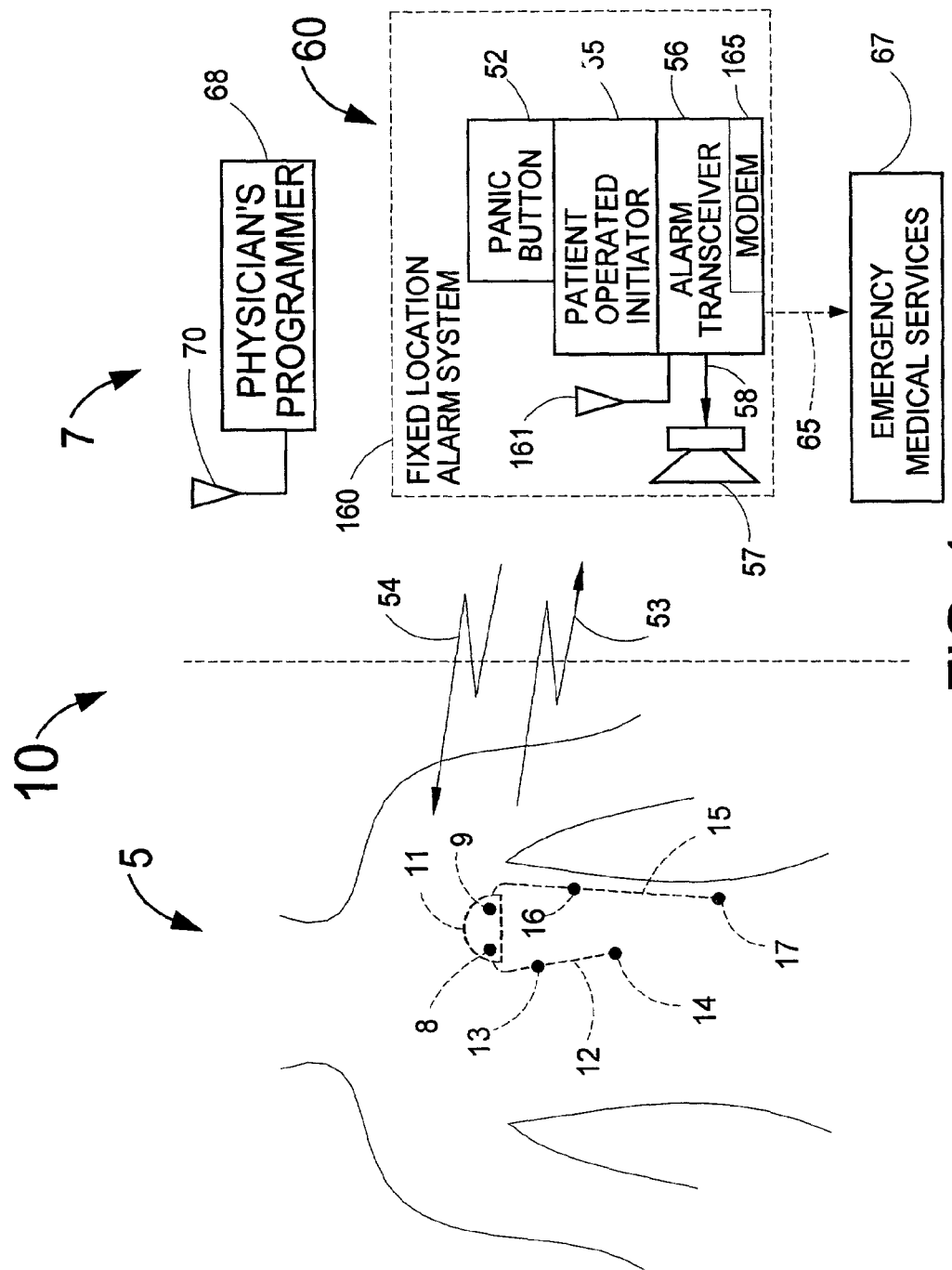
FIG. 1 illustrates a cardiosaver system for the detection of a cardiac event and for warning the patient that a cardiac event is occurring.

FIG. 1 illustrates one embodiment of the cardiosaver system 10 consisting of an implanted medical device 5 which is a cardiosaver 5 and external equipment 7. The cardiosaver 5 consists of an electronics module 11 that has two leads 12 and 15 that have multi-wire electrical conductors with surrounding insulation. The lead 12 is shown with two electrodes 13 and 14. The lead 15 has electrodes 16 and 17. In fact, the cardiosaver 5 could utilize as few as one lead or as many as three and each lead could have as few as one electrode or as many as eight electrodes. Furthermore, electrodes 8 and 9 could be placed on the outer surface of the electronics module 11 without any wires being placed externally to the electronics module 11.

The lead 12 in FIG. 1 could advantageously be placed through the patient's vascular system with the electrode 14 being placed into the apex of the right ventricle. The electrode 13 could be placed in the right ventricle or right atrium or the superior vena cava. It is also anticipated that the lead 15 could be placed into the venous circulation of the myocardium. If electrodes 16 and/or 17 are placed into a vein, such as the coronary sinus or any other vein of the myocardium, then even a comparatively limited ischemic area of that region of the myocardium would produce a distinct electrogram indicating the early onset of a heart attack. The metal case of the electronics module 11 could also serve as an indifferent electrode with either or both electrodes 13 and/or 14 being active electrodes. It is also conceived that the electrodes 13 and 14 could be used as bipolar electrodes. The placement and function of the lead 12 could be similar to that which is well known for leads used with heart pacemakers or defibrillators (ICDs).

The lead 15 could advantageously be placed subcutaneously at any location where the electrodes 16 and/or 17 would provide a good electrogram signal indicative of the electrical activity of the heart. Again for this lead 15, the case of the electronics module 11 could be an indifferent electrode and the electrodes 16 and/or 17 could be active electrodes or electrodes 16 and 17 could function together as bipolar electrodes. The cardiosaver 5 could operate with only one lead and as few as one active electrode with the case of the electronics module 11 being an indifferent electrode. The cardiosaver system described herein can readily operate with only two electrodes.

The electronics module 11 contains a battery and electronic circuitry that can warn the patient when an acute myocardial infarction or an arrhythmia is occurring, can store for later readout the patient's electrogram, and can send wireless signals 53 to and receive wireless signals 54 from the external equipment 7. The functioning of the electronics module 11 will be explained in greater detail with the assistance of FIG. 6.

FIG. 1 also shows the external equipment 7 that consists of an external alarm system 60 and a physician's programmer 68 having an antenna 70. The physician's programmer 68 can advantageously be a laptop computer that is programmed with specific software to interact with the implanted cardiosaver 5. When a laptop computer is used for this purpose it would have a receiver for receiving a wireless signal from the cardiosaver 5 and a transmitter for sending a wireless signal to the cardiosaver 5. The screen on the laptop would be used to provide guidance to the physician in communicating with the cardiosaver 5. Also, the screen would be used to display both real time and stored electrograms that are read out from the cardiosaver 5.

In FIG. 1, the external alarm system 60 includes emergency medical services 67 and a fixed location alarm system 160 having a patient operated initiator 55, an alarm transceiver 56, an alarm speaker 57 and an antenna 161. The alarm transceiver 56 of the fixed location alarm system 160 connects to the outside world through a telephone link 65. The telephone link can be either a fixed or wireless telephone connection that allows the alarm transceiver 56 to call out to emergency medical services 67. The typical fixed location alarm system 160 would be built into a cordless phone with a base station/charging stand that connects to a standard telephone line that acts as the telephone link 65. A modem 165 integrated into the alarm transceiver 56 is used to send over the telephone link 65 the alarm detected and the electrogram data sent out from the implanted cardiosaver 5.

The purpose of the patient operated initiator 55 is to give the patient the capability for initiating the holding in the memory of the implanted cardiosaver a particular electrogram that the patient wishes to have shown to his doctor. A separate "panic button" 52 might be part of the patient operated initiator 55. The panic button 52 of the patient operated initiator 55 could be pressed by the patient to cause the alarm transceiver 56 to initiate a call to emergency medical services 67 or to a medical practitioner at a remote location in the event the patient feels that he is undergoing a cardiac event. If such an event occurs, the patient may request advice from the medical practitioner at a diagnostic center or from his own personal physician to determine what he should do. For example, the patient might feel a flutter in his chest from an atrial fibrillation and he may wish to seek advice from a trained medical practitioner as to what he should do. When the patient operated initiator 55 is activated, a command is sent by the signal 54 to the electronics module 11. When the command is received by the electronics module 11, the patient's stored and/or real time electrogram could be transmitted from the implanted cardiosaver 5 to the alarm transceiver 56 and then by the alarm transceiver 56 over the telephone link 65 to a remote medical practitioner. The remote medical practitioner could then analyze the electrogram data and call the patient back to offer advice as to whether this is an emergency situation or the situation could be routinely handled by the patient's personal physician at some later time.

The purpose of the physician's programmer 68 shown in FIG. 1 is to change the operating parameters of the implantable cardiosaver 5 and to read out data stored in the memory of the electronics module 11 such as stored electrograms. This would be accomplished by sending a programming wireless signal 54 to the cardiosaver 5 and receiving telemetry by the wireless signal 54 from the cardiosaver 5.

The purpose of the alarm transceiver 56 is to receive over the antenna 161 wireless signals 53 from the electronics module 11 of the implanted cardiosaver 5 indicating the detection of a cardiac event and to warn the patient by an audio signal 58 sent to the al&ar speaker 57. The audio signal 58 could be a sequence of tones and/or a speech message that instructs the patient as to what actions should be taken. Furthermore, the alarm transceiver 56 can, depending upon the nature of the signal 53, place an outgoing call over the telephone link 65 to summon emergency medical services 67. When the detection of an acute myocardial infarction is the cause of the alarm, the alarm transceiver 56 would automatically notify the emergency medical services 67 that a heart attack has occurred and an ambulance could be sent to treat the patient and to bring him to a hospital emergency room.

When an alarm is sent within the signal 53 that indicates that a cardiac event is occurring, the modem 165 dials out and sends a message over the telephone link 65 to the emergency medical services 67. The message sent over the telephone link may include the following information: (1) a specific patient is having an acute myocardial infarction or other cardiac event, (2) the patient's name, address and a brief medical history, (3) a map and/or directions to where the patient is located, (4) the patient's stored and real time electrogram, and (5) a prescription written by the patient's personal physician as to the type and amount of drug to be administered to the patient in the event of a heart attack. If the emergency medical services include an emergency room at a hospital, information can be transmitted that the patient is in a car and on his way to the emergency room. In this manner the medical practitioners at the emergency room could be prepared for the patient's arrival.

Figure 6:
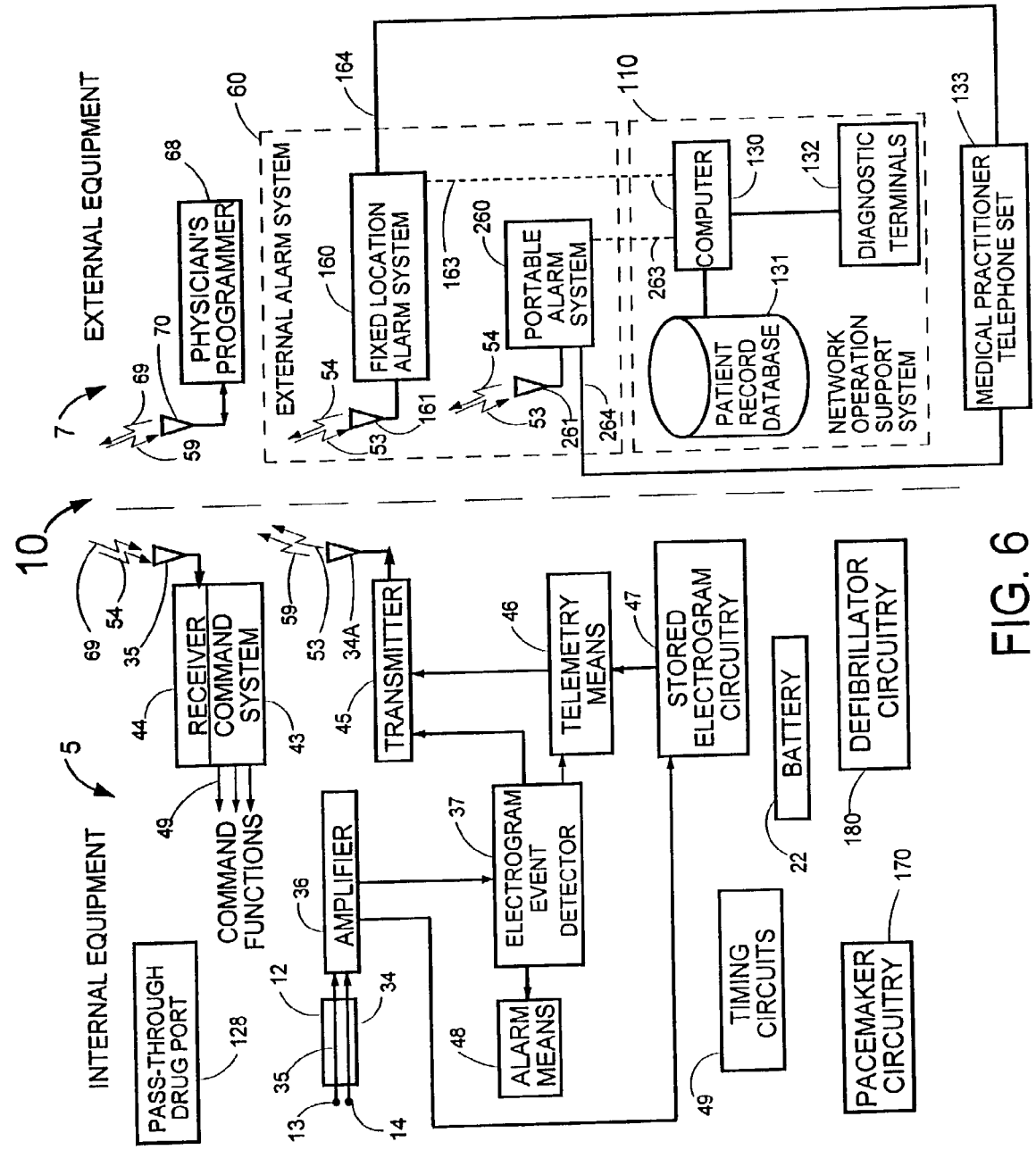
FIG. 6 is a block diagram of the cardiosaver system that illustrates the implantable and external portions of the system.
Figure 8:
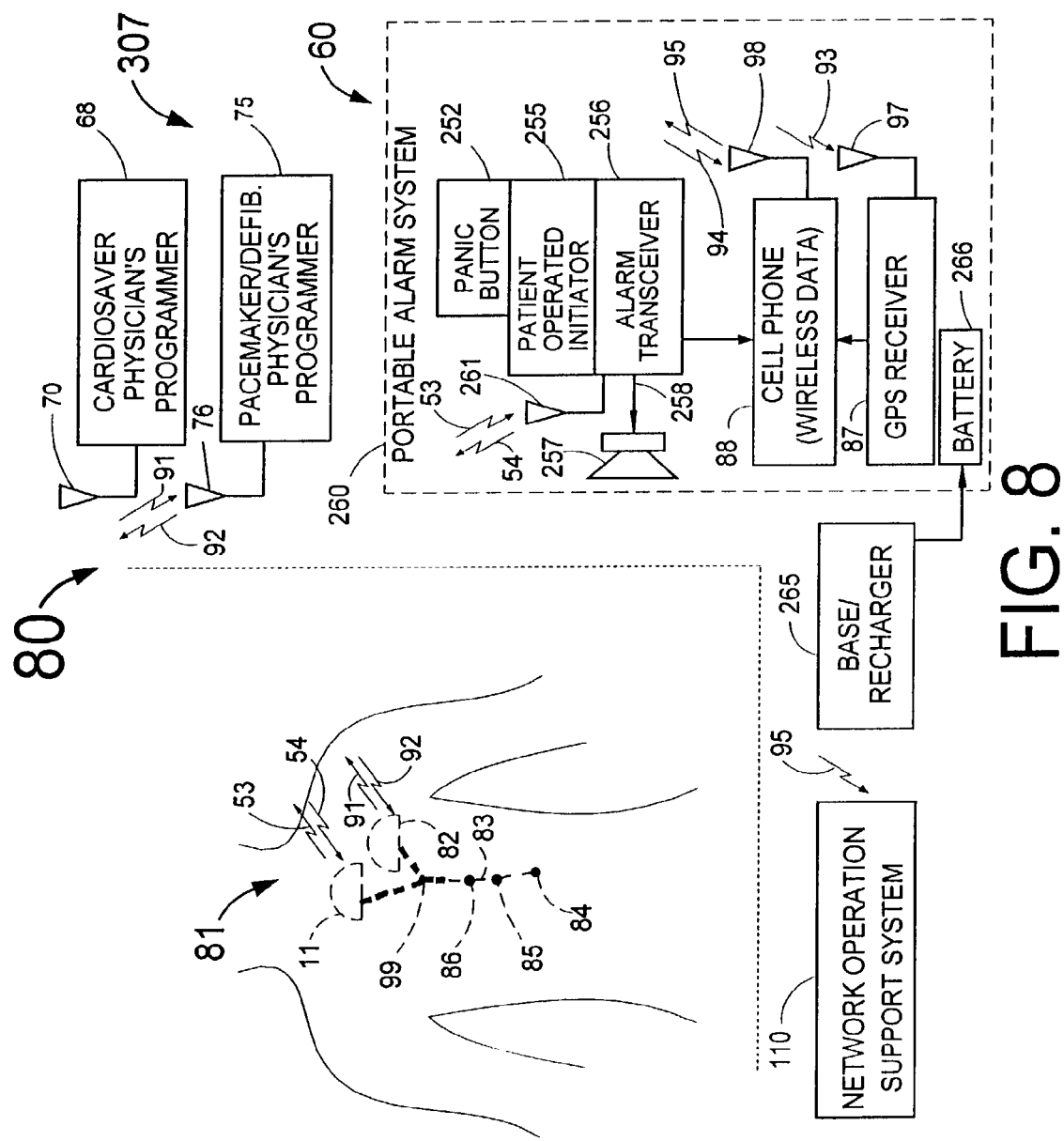
FIG. 8 illustrates an implanted cardiosaver device with a portable external system and a separate pacemaker or ICD joined to the cardiosaver by a "Y" electrical connector.

A portable version of the external alarm system 60 is discussed with the aid of FIGS. 6 and 8. The functions of each portion of the external equipment 7 are explained in greater detail with the aid of FIGS. 6 and 9.

Figure 2:
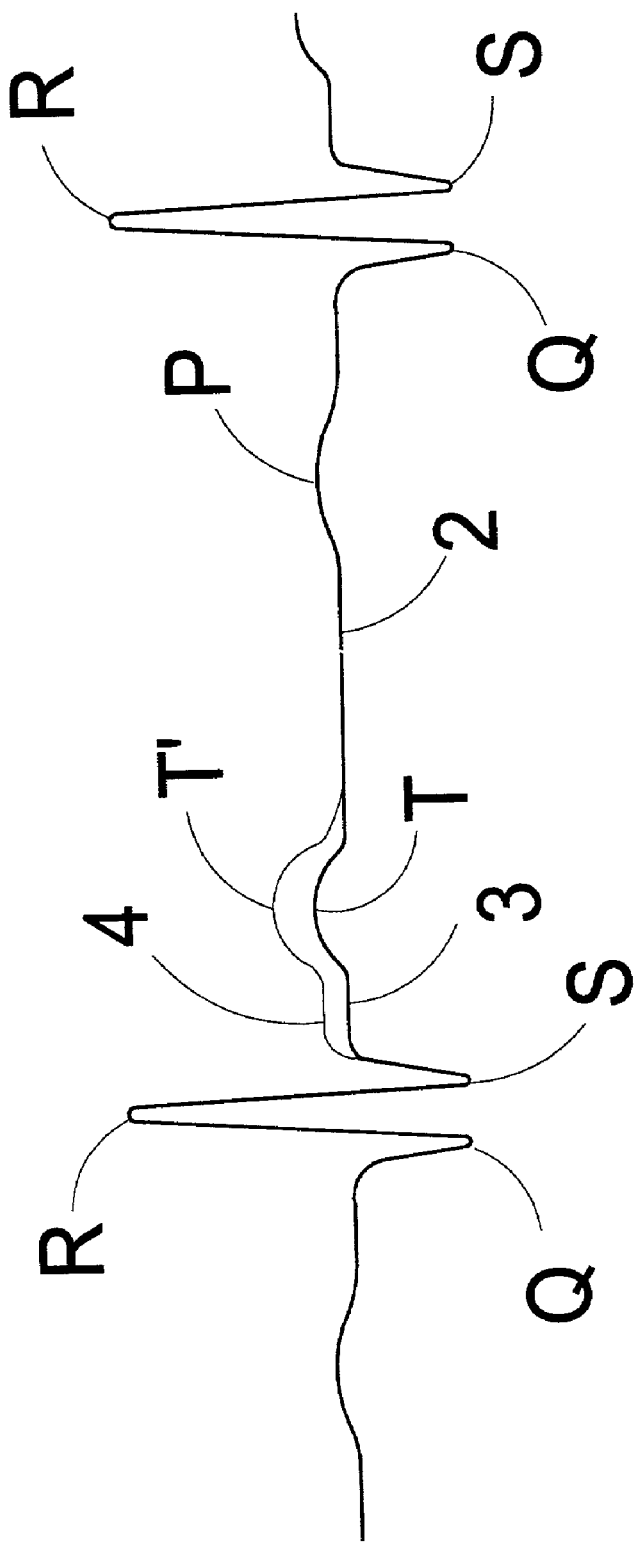
FIG. 2 illustrates a normal electrogram pattern and also shows an elevated ST segment that would be indicative of an acute myocardial infarction.

FIG. 2 illustrates a typical electrogram signal from some pair of implanted electrodes such as the electrode 14 and the case 18 of FIG. 3. The various portions of the electrogram are shown as the Q, R, S, T and P waves. These are all shown as portions of a heavy solid line in FIG. 2. The normal ST segment 3 is also shown in FIG. 2. When an acute myocardial infarction occurs, there is typically an elevation (or depression) of the ST segment 4 as shown by the light solid line in FIG. 2. It is this deviation of the ST segment 4 (T') as compared to the undeviated segment 3 (T) that is a clear indicator that an acute myocardial infarction is occurring in a significant portion of the patient's myocardium. Although an elevated ST segment 4 can be a good indicator of an acute myocardial infarction, other indicators such as a sudden change of heart rate or heart wall motion, intra-coronary blood pressure or a sudden decrease in blood $pO_2$ could also be used as independent sensing means or those signals could be used in addition to the voltage deviation of the ST segment 4. It is important to note that the electrogram from implanted electrodes will provide a faster detection of an ST segment shift as compared to an ECG signal obtained from skin surface electrodes. Thus the electrogram from implanted electrodes as described herein is an ideal means for the earliest detection of a heart attack.

It is anticipated that when a patient who has a stenosis in a coronary artery is performing a comparatively strenuous exercise his heart rate increases and he can develop coronary ischemia that can result in a deviation of the ST segment of his electrogram. This is particularly true for patients who have undergone balloon angioplasty with or without stent implantation. Such patients will be informed by their own physician that, if their cardiosaver activates an alarm during exercise, that it may be indicative of the progression of an arterial stenosis in one of the heart's arteries. Such a patient would be advised to immediately seek medical care as the event would probably be an emergency if there were other symptoms of a heart attack, but would probably be indicative of a non-emergency condition (namely the progression of a stenosis) if there were no symptoms of a heart attack. As previously described, the implanted cardiosaver device could emit a different signal if there is a heart attack as compared to the signal that would be produced if there were ischemia resulting from exercise. It is envisioned that heart rate and the rate of change of heart rate experienced during an ST segment voltage deviation can be used to indicate which alarm should be produced by the cardiosaver. Specifically, an ST segment deviation at a near normal heart rate would indicate an acute myocardial infarction. An ST segment deviation when there is an elevated heart rate (e.g., greater than 100 bpm) would generally be indicative of a progressing stenosis in a coronary artery. In any case, if a sufficient ST segment deviation occurs that results in an alarm from the cardiosaver, the patient should promptly seek medical care to determine the cause of the alarm.

The method to determine if the patient has a stenosis in a coronary artery that is becoming progressively more narrowed would be as follows:

a) implanting a stent into a patient's coronary artery;
b) implanting a cardiosaver device into that same patient;
c) advising the patient to seek medical care if the cardiosaver device alarms the patient during exercise.

It should be understood that, depending on a patient's medical condition, a vigorous exercise might be as energetic as running a long distance or merely going up a flight of stairs. After the cardiosaver is implanted in a patient who has undergone a stent implant, he should have a stress test to determine his level of ST segment shift that is associated with the highest level of exercise that he can attain. The patient's heart rate should then be noted and the cardiosaver should be programmed to not alarm at slightly below that heart rate for that observed level of ST segment deviation. Then if at a later time the patient experiences an increased deviation of his ST segment at that pre-determined heart rate, then an alarm indicating ischemia can be programmed to occur. The occurrence of such an alarm can indicate that there is a progression in the narrowing of some coronary artery that may require angiography to determine if angioplasty, possibly including stent implantation, is required. If however, this same ST segment deviation occurs at a normal heart rate, then the alarm for an acute myocardial infarction would be produced and an emergency situation would exist for the patient to obtain treatment for that condition.

The alarm signal associated with a significant ST segment deviation caused by an acute myocardial infarction can be quite different from the alarm means associated with progressing ischemia during exercise. For example, during exercise the alarm signal might be an audio signal that occurs for 10 seconds every 30 seconds. A different alarm signal, for example an audio signal lasting for 1 to 3 seconds every 5 to 10 seconds, may be used to indicate an acute myocardial infarction. In any case, a patient can be taught to recognize which signal occurs for these different circumstances so that he can take immediate response if an acute myocardial infarction is indicated but can take a non-emergency response if progression of the narrowing of a stenosis is indicated. It should be understood that other distinctly different audio alarm patterns could be used for different arrhythmias such as atrial fibrillation, atrial flutter, PVC's, PAC's, etc. A capability of the physician's programmer 68 of FIG. 1 would be to enable or disable alarms in the implanted cardiosaver for any one or more of these various cardiac events. Also, the intensity of the audio alarm, vibration or electrical tickle alarm could be adjusted to suit the needs of different patients.

FIG. 3 is a plan view of the implanted cardiosaver 5 showing the electronics module 11, having a battery case 18, an electronics section case 19 and a header 20. Electrical conductors placed through the plastic header 20 connect the electronics module 11 to the electrical leads 12 and 15, which have respectively electrodes 13 and 14 and 16 and 17. The on-case electrodes 8 and 9 of FIG. 1 are not shown in FIG. 3. It should also be understood that the cardiosaver 5 can function with only two electrodes, one of which could be the case 18 or 19. All the different configurations for electrodes shown in FIGS. 1 and 3, such as the electrodes 8, 9, 13, 14, 16 or 18 or the metal case 18 or 19 are shown only to indicate that there are a variety of possible electrode arrangements that can be used with the cardiosaver 5.

The metal case 19 of the electronics section of the electronics module 11 is joined to the metal battery case 18 by a weld 21. On the metal case 19, a conducting disc 31 mounted onto an insulating disc 32 can be used to provide a subcutaneous electrical tickle to warn the patient that an acute myocardial infarction is occurring.

FIG. 4 is a cross section of the electronics module 11 at section 4—4 of FIG. 3. Shown in FIG. 4 is the battery 22 within the metal case 18 and having an end metal plate 23. The metal case 19 encloses the electronics section 24 that has a plastic header 20 within which electrical connections can be made to the leads 12 and 15. Also shown in FIG. 4 is the cross section of the electrical tickle device consisting of the insulator disc 32 through which a wire 33 connects to the conducting disc 31. When an alternating voltage is applied between the conducting disc 31 and the metal case 19, the patient will experience a subcutaneous electrical tickle that can serve as a warning that some pre-programmed heart condition has been detected. The weld 21 can be used to hermetically seal the battery case 18 to the case 19 of the electronics section 24. Also shown in FIG. 4 (and in FIG. 5) is a sound or mechanical vibration source 6 (typically in the form of a piezoelectric crystal) that can provide an audio or mechanical vibration signal that can be detected by the patient or, for an audio source, by a person nearby. Such an alarm would be an indication that an acute myocardial infarction or some other cardiac event is occurring. This source 6 would typically be a piezoelectric device that produces a sound that can be readily heard. The level of intensity of either the electrical tickle, vibration or the audio signal would be able to be programmed by the patient's physician to a level that is clearly observable but not disturbing or painful. A typical duty cycle for such a signaling device would be an on-time of approximately 1 to 5 seconds and an off-time for a time period between approximately 10 and 60 seconds. It is anticipated that the on-time and off-time could be programmed by the patient's physician. It is further anticipated that the warning signal when the patient's heart rate indicates he is performing an exercise can be different from the signal when an acute myocardial infarction is detected which is associated with a more moderate heart rate. As one example of such two different signals, when the patient's heart rate exceeds 120 beats per minute (bpm), it is reasonable to assume that the patient is exercising. At the 120-bpm heart rate, if a deviation of the ST segment is observed, the patient might experience an alarm on-time that occurs for a longer or shorter time and/or a longer or shorter off-time as compared to those times when the heart rate is below 100 bpm. Thus the patient and the diagnostic center medical practitioner could differentiate between a typical acute myocardial infarction and ischemia resulting from the progression of a coronary artery stenosis. Other unique alarms could be programmed for a variety of cardiac events such as atrial or ventricular fibrillation.

FIG. 5 is a cross section of the electronics module 11 at section 5—5 of FIG. 4. In FIG. 5, the case 18 and the end metal plate 23 form a hermetically sealed enclosure for the battery 22. By this construction of having the battery case 18 formed as part of the case of the electronics module 11, a reduced thickness for the electronics module 11 can be accomplished. It is also envisioned that the battery 22 could be a separate device that is placed inside of a separate case of the electronics module 11.

FIG. 5 also shows a battery feed-thru 25 having a terminal 26 that is one terminal of the battery 22, the other terminal being the battery case 18. Going through the case 19 of the electronics module 24 are two feed-thrus 27 and 29 through which electrical connections are made respectively to the wire 28 of the lead 12 and the wire 30 of the lead 15. The feed-thrus 27 and 29 and the wires 28 and 30 are encapsulated in the plastic of the header 20. It should be understood that, if there are multiple electrodes in a lead, there must be more than one wire in that lead that passes through the header 20 and electrically connects to the electronics section 24. Furthermore, it should be understood that any lead attached to the electronics module 11 could be a detachable lead as is currently used with pacemakers and ICDs.

FIG. 6 illustrates in the form of a block diagram the entire cardiosaver system 10 consisting of the internal equipment which is the implanted cardiosaver 5 and the external equipment 7. The left side of FIG. 6 shows portions of the system that would be implanted in a patient who has a comparatively high probability for having a cardiac event such as an acute myocardial infarction or he has an implanted stent and the cardiosaver is implanted to provide an indication of the progression of narrowing of a coronary artery. These would be patients who have one of the following conditions:

1. They have survived a first heart attack,
2. They have survived a first stroke,
3. They have an implanted pacemaker or defibrillator,
4. They have atherosclerotic disease or have had bypass surgery or have a family history of heart disease,
5. They have had angioplasty or an implanted stent,
6. They are elderly patients who have diabetes,
7. They have any other condition that is associated with a reasonably high probability of having a heart attack or a stroke.

FIG. 6 shows the electrodes 13 and 14 connected to an amplifier 36 by the wires 34 and 35 in the lead 12 that would be typically placed into the apex of the right ventricle. It should be understood, however, that the implanted electrodes and the lead could be outside the heart or the electrodes could be mounted onto the case of the electronics module 11 or one electrode could be the case itself. It is important to note that the cardiosaver system 10 can operate with as few as two electrodes. However, the cardiosaver 5 could utilize as many as eight different implanted electrodes that are situated at different locations either inside or outside the heart. The object of having electrodes at different locations would be to have a significant ST segment voltage deviation for an infarct that might occur in a different part of the heart. For example, the greatest ST segment voltage deviation for an obstruction of the right coronary artery might occur at a different location as compared with an obstruction of the left anterior descending artery of the heart. In all cases, it is desirable to sense the maximum possible ST segment voltage change caused by an arterial obstruction. The implanted cardiosaver 5 can be programmed by a wireless signal from the physician's programmer 68 to detect the maximum ST segment voltage deviation from one of a multiplicity of electrodes and then indicate to an outside source which electrode has detected the maximum signal. The electrode placement could then be related by a trained medical practitioner to the region in the heart where the infarction has occurred.

Returning now to FIG. 6, the amplified electrogram signal from the amplifier 36 is fed into the electrogram event detector 37 and the stored electrogram circuitry 47. The electrogram event detector 36 has the capability to detect and differentiate between an acute myocardial infarction, ischemia caused by exercise at an elevated heart rate, or a variety of pre-programmed arrhythmias that are enabled for detection using the physician's programmer 68 of the external equipment 7. Although FIG. 6 shows only one channel of an amplifier, it should be understood that as many as eight channels for detecting electrogram signals could be used. The electrodes for each such channel would be positioned inside or outside the heart to obtain an optimum electrogram signal for determining an obstruction from some particular coronary artery. When an ST segment voltage deviation is detected by the electrogram event detector 37 for at least one channel of the cardiosaver, an implantable alarm means 48 causes a subcutaneous electrical tickle, vibration or an audio warning signal to be produced that warns the patient that an acute myocardial infarction or some other heart problem is occurring. Of all these alarms, an audio signal would have the greatest advantage because it can be heard by a caretaker as well as by the patient.

When an ST segment deviation is detected, the stored electrogram circuitry 47 holds a previous time period of electrogram recording in a digital, solid state memory and then proceeds to record an additional time period of the patient's electrogram. The previous time period could be as short as 10 seconds or as long as 10 minutes. The additional time period could be as short as one minute or as long as 10 minutes.

One method to determine if an acute myocardial infarction has occurred is to determine the average voltage of the ST segment compared to some reference voltage of the electrogram for a fixed number, N, of heart beats. Then at some predetermined later time, T, the average voltage of the ST segment is measured again for this same number N of heart beats. When a predetermined deviation of the ST segment voltage is observed over that time period, the cardiosaver will be programmed to cause an alarm. For example, if we take N=8 and T=100 seconds, it could be expected that there would be a sufficient change in voltage of the ST segment to detect an acute myocardial infarction in that time period. It should be understood that N is ideally greater than 2 and less than 100. Furthermore, T is ideally at least 15 seconds and certainly less than 300 seconds.

Another method for determining if an acute myocardial infarction is occurring is to program the cardiosaver to observe if there is some averaged ST segment voltage deviation that is less than that signifying a heart attack but more than would be normally expected for that heart rate. If such an intermediary level of average ST segment voltage is observed, the logic of the cardiosaver could then compare that average ST segment voltage with the measured value at a time –T or –2T. If that comparison indicated a sufficient average ST segment voltage deviation corresponding to an acute myocardial infarction, then an alarm for an acute myocardial infarction could be made to occur. As an example, let us say that a deviation of 4 millivolts (mv) in the average value of the ST segment voltage is necessary to cause an alarm but a deviation between successive voltage measurements of only 2 mv is sufficient for the logic to look back in time to T=–100 seconds. Let us then say that at time T=0 we observed a voltage deviation of 2 mv compared with voltage at T=–100 seconds. Then at time T=+100 seconds we observed an average ST segment voltage deviation of 3 mv compared to the measured value at T=0. The logic of the cardiosaver could be programmed to then compare the average ST segment voltages at T=+100 seconds with the value at T=–100 seconds which difference is 5 mv which is sufficient to cause an alarm to occur. This methodology can be used to reduce the number of acute myocardial infarction events that might go undetected. Furthermore, this methodology would allow detection of an acute myocardial infarction to occur in a shorter period of time. This would decrease the time between the onset of a heart attack and the arrival of medical personnel to treat that heart attack or the time required to get the prescribed medication from a storage place and inject it into the patient by the patient himself or by a caretaker.

Returning now to other internal equipment which forms the cardiosaver 5 shown in FIG. 6, the timing circuits 49 would provide all the timing signals required for the operation of the implanted equipment 5 including a real time clock for marking the time of incidence of detected cardiac events, and the battery 22 would provide the electrical power to operate all parts of the cardiosaver 5. A separate or a pass-through drug port 128 that is integrated into the cardiosaver 5 could be used to deliver medication directly into the patient's bloodstream. The use of such separate or integrated drug ports is explained in detail with the assistance of FIGS. 7 and 10–15.

The right side of FIG. 6 illustrates components of the cardiosaver system 10 that would be situated externally to the patient. There are three primary components of the external equipment 7, namely: a physician's programmer 68 with antenna 70, an external alarm system 60 and a network operation support system 110. The physician's programmer 68 is typically located at the office of the patient's physician. The external alarm system 60 can be a fixed location alarm system 160 at a location where a patient spends most of his time, or a portable alarm system 260 that the patient can carry with him. For example, the fixed location alarm system 160 could be placed at the patient's home or in a nursing home where the patient is living and would typically operate through a standard telephone line. The portable alarm system 260 would operate though a wireless telephone network like a cell phone. The network operation support system 110 includes at least one centrally located computer 130 having a patient record database 131 and diagnostic center terminals 132. The network operation support system 110 would be located at one or more centrally located network operation centers that would have high reliability through backup power and other features of a telephone services central office. The diagnostic center terminals 132 would be situated at one or more diagnostic centers where medical practitioners could respond to incoming cardiac event alarms.

When the electrogram event detector 37 detects any electrogram signal for which it is programmed to alarm, the transmitter 45 is turned on which causes a wireless signal 53 indicating the detection of a cardiac event to be transmitted out of the antenna 34A, which could be the wire 34 in the lead 12, or it could be a separate antenna. The signal 53 is received by the antenna 161 of the fixed location alarm system 160 and/or the antenna 261 of the portable alarm system 260 both of which are external alarm systems 60 of the external equipment 7. The fixed location alarm system 160 or the portable alarm system 260 is each capable of emitting an audio alarm to warn the patient that an acute myocardial infarction (or some other heart problem) is occurring. The audio alarm could be a loud ringing sound, or preferably a voice would inform the patient that: (1) his implanted equipment indicates that he may be having a heart attack or some other cardiac event; (2) he should take some previously agreed upon medication(s) such as aspirin or even be injected with a thrombolytic or anti-thrombogenic agent such as tPA or heparin; (3) an emergency rescue service has been called; and (4) he should either immediately go to a hospital emergency room or he should wait for an ambulance to come with paramedics who are trained to treat cardiac events such as a heart attack. Additionally, the alarm could include a flashing light and/or text directions for the patient to follow.

The fixed location and portable alarm systems 160 and 260 respectively have the capability to send and receive data signals 163 and 263 respectively to and from the computer 130 of the network operation support system 110 located at a network operation center. These data signals 163 and 263 may be produced by a modem and sent over voice telephone connections or they may originate as data packets and be transmitted over a digital data network such as the Internet. The fixed location and portable alarm systems 160 and 260 respectively also have the capability to send and receive voice telephone calls 164 and 264 respectively to and from a medical practitioner telephone set 133 at a diagnostic center. This capability is used when the medical practitioner sees an incoming alarm placed by the computer 130 on one of the diagnostic terminals 132 and uses the medical practitioner telephone set 133 at a diagnostic center to call the patient back either on the patient's home phone or on the built-in telephone which is part of the fixed location alarm system 160 or the portable alarm system 260.

In addition to the incoming alarm displayed on the diagnostic terminal 132, the computer 130 will also display the medical record of the patient from the patient record database 131.

The implanted alarm means 48 would typically be a sound, vibration or electrical tickle that had a duration of a few seconds and would be turned on approximately every 5 to 60 seconds over a time period of approximately 15 to 30 minutes. The physician's programmer 68 would have the capability of adjusting the intensity of the audio alarm, the level of vibration, and/or the intensity of the subcutaneous electrical tickle so that such an alarm is clearly discernible by the patient. The physician using the physician's programmer 68 could train each patient to recognize some clearly discernible signal as an indication that the patient should immediately seek medical assistance. The physician's programmer 68 would also have the capability to enable or disable the implanted alarm means 48. The physician's programmer 68 might optimally be a lap top computer that includes a wireless system for interacting with the implanted cardiosaver 5.

Returning now to a discussion of the cardiosaver system 10, an electrogram stored in the stored electrogram circuitry 47 as well as other device status information for the implanted cardiosaver 5 could be sent via the transmitter 45 by means of a wireless signal 59 to the physician's programmer 68. The wireless signal 59 arriving through the antenna 70 and into the physician's programmer 68 would allow a physician to study the patient's electrogram and also receive other telemetry data such as battery voltage of the battery 22 inside the cardiosaver 5. Additional data from the cardiosaver 5 would include (but is not limited to) the status of how each alarm generated by the alarm means has been programmed to respond to different cardiac events and the length of time programmed for retaining prior electrogram data when a cardiac event occurs. The physician's programmer 68 can also receive real time (as well as stored) electrogram data over the wireless signal 59.

The physician's programmer 68 can send a wireless signal 69 out of its antenna 70 to the receiver 44 of the command system 43. These command signals could cause various command functions 49 to take place. For example, one command function 49 would be to change the threshold voltage level of the ST segment deviation that indicates by means of the electrogram event detector 37 that a heart attack has started. Another command could set the number N of heartbeats that would be used in the computation of the average value of the ST segment voltage. Other command functions 49 could be used to adjust the intensity or the pattern of the audio alarm or subcutaneous tickle that warns the patient that some heart problem is occurring. Still another set of command functions would be to select which electrode(s) for electrogram voltage detection should be enabled. Still another set of command functions could adjust the time periods for the stored electrogram 47. For instance the time period for storing data prior to the detection of an acute myocardial infarction could be changed from 15 seconds to 60 seconds. This type of programming is well known in the art of heart pacemakers and implantable defibrillators.

The fixed location alarm system 160 would be placed where the patient would spend most of his time. Typically this would be at his home, although it could also be at another site such as an assisted living apartment or a nursing home. The distance from the cardiosaver 5 to the close fixed location alarm system 160 should be less than 200 meters. It is also envisioned that the patient might carry or have placed on his body or in his clothing a repeater (specifically the repeater 77 of FIG. 7) that could receive a comparatively short range signal from the implanted cardiosaver 5 and relay that wireless signal to the fixed location alarm system 160. The repeater 77 could be worn on the patient's belt or be built into a pendant worn around the patient's neck.

If the start of an acute myocardial infarction is indicated, the patient could be aroused, even from sleep, by sounds emitted from the alarm speaker 57 of the fixed location alarm system of FIG. 1. The patient could then prepare for an emergency medical services ambulance to come to his home to take him to an emergency care facility. It is also conceivable that the patient's caretaker could take the patient to an emergency facility for treatment without waiting for the ambulance to arrive. If this were done, some simple means to inform the rescue service to not send an ambulance could be accomplished by telephone or by other means within the external equipment 7. Furthermore, it is anticipated that the patient may have at his home an external heart defibrillator system. If the patient has a heart attack that sounds the alarm from the alarm speaker 57 and the patient is unconscious because of ventricular fibrillation, then a caretaker might hear (or be awakened by) the alarm and could apply voltage pulses from the defibrillator so as to save the patient's life.

Figure 7:
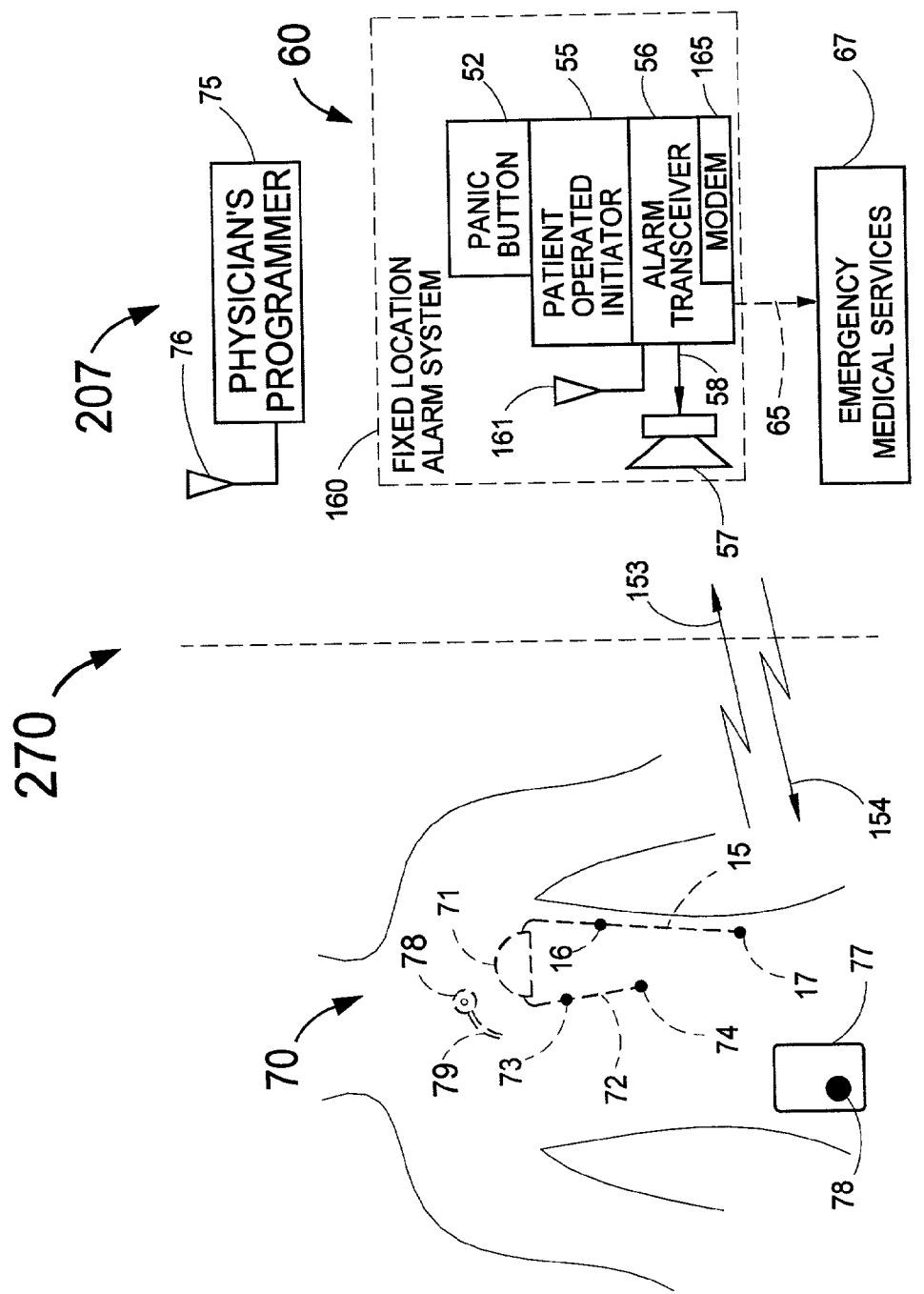
FIG. 7 illustrates a cardiosaver system that includes a device with cardiosaver capability plus a separate drug port.

Although the cardiosaver system 10 as described herein could clearly operate as a stand-alone system, it is clearly conceivable to utilize the cardiosaver system 10 with a defibrillator or pacemaker (including a biventricular pacemaker for congestive heart failure). As shown in FIG. 6, pacemaker circuitry 170 and/or defibrillator circuitry 180 could be made part of any implanted cardiosaver device 5. The circuitry for the implanted portion of the cardiosaver system 10 could also be included within the electronics section of such a pacemaker or defibrillator (as seen in FIG. 7). Furthermore, two separate devices (one pacemaker or one defibrillator plus one cardiosaver) could be implanted within the same patient. Still further, the cardiosaver 5 having a capability of a pacemaker 170 or a defibrillator 180 could be used with a separate or an integrated pass-through drug port.

FIG. 7 shows a pacer-cardiovertor-cardiosaver system 270 consisting of an implanted pacercardiovertor-cardiosaver 70 and external associated equipment 207. A pacer-cardiovertor is defined herein as the electronic circuitry for either a pacemaker or a defibrillator or the circuitry that can both pace and/or defibrillate a heart. The implanted pacer-cardiovertor-cardiosaver 70 consists of a single electronics module 71 that contains combined pacemaker and cardiosaver electronic circuitry, combined defibrillator and cardiosaver electronic circuitry or all three capabilities together. The lead 72 is placed in the patient's circulatory system; specifically, the electrode 74 is typically situated in the right ventricle near the apex of the heart, and an electrode 73 can be placed in the superior vena cava or in the right atrium or ventricle. It is further envisioned that the lead 72 could have as many as eight electrodes at different locations for optimizing the sensing of ST segment voltage deviations for obstructions of the different coronary arteries. Each such separate or each pair of such electrodes could be a separate channel for ST segment voltage deviation measurement or for the measurement of other electrogram signals indicating various cardiac events. The electrode 74 could be an active electrode and a metal case of the electronics module 71 could serve as an indifferent electrode. The lead 72 with electrodes 73 and 74 could also be used for the cardiosaver portion of the electronics module 71. Alternatively, a separate lead 15 having electrodes 16 and 17 could be used by the cardiosaver portion of the electronics module 71 in exactly the same way as has been described for the cardiosaver system 10 of FIG. 1. As is the case for the lead 72, the lead 15 could have more than two electrodes with each separate or pair of electrodes being optimally placed for detecting the ST segment voltage deviation from a particular coronary artery. The fixed location system 160 including its antenna 161, telephone link 65 and emergency medical services 67 would also function as described for FIGS. 1 and 6. However, the physician's programmer 75 of FIG. 7 having an antenna 76 would be used somewhat differently. The physician's programmer 75 differs from the physician's programmer 68 of FIGS. 1 and 6 in that it would also have the capability for interacting with the pacer-cardiovertor portion as well as the cardiosaver portion of the electronic circuitry within the electronics module 71. Adding cardiosaver capability to existing pacemakers and/or defibrillators would make either of those devices more valuable in prolonging the life of a human patient in whom such a combined system is implanted. As described below with the assistance of FIGS. 10–13, a subcutaneous drug port 78 and medication delivery catheter 79 could be used with a pacer and/or defibrillator that may or may not include a cardiosaver capability. Such a drug port 78 can be used for patient self-administration, caretaker, or medical practitioner injection of therapeutic drug(s) into the patient's bloodstream. It is also envisioned that the separate drug port 78 with medication delivery catheter 79 could be implanted with the cardiosaver 5 of FIG. 1 when there is no associated pacemaker or defibrillator.

FIG. 7 also shows a repeater 77 that can be worn or carried by the patient. Such a device would receive a low-level wireless signal from the implanted cardiosaver circuitry and it could respond in two different modes. One mode would be to immediately inform the patient by a comparatively loud human voice message or other sound that an acute myocardial infarction or other cardiac event has been detected and that he should take some medication and/or immediately proceed to an emergency medical facility. The other mode is to act as a repeater to relay wireless signals 153 and 154 to and from respectively the fixed location alarm system 160. The advantage of the repeater 77 is that it can be kept with the patient wherever he might be in or near the patient's primary location. Also, being in very close proximity to the source of the wireless signal from the implanted cardiosaver 70 makes it easier to pick up the signal indicating that a cardiac event is occurring. The repeater 77 could be placed in a pocket, worn on a belt, placed into a pendant hung around the neck or located in a special vest-like device placed somewhere on the body of the patient.

The repeater 77 would also have a panic button 78 that would activate the same actions as the panic button 52 of the fixed location alarm system 160 described previously in the explanation of FIG. 1.

FIG. 8 illustrates a cardiosaver system 80 in which the implant 81 includes a cardiosaver electronics module 11 and an implanted pacemaker or defibrillator 82. In this embodiment, the electronics module 11 has a lead 83 having individual electrodes 84, 85 and 86 that also provide signals to an implanted pacemaker or defibrillator 82. The cases of the electronics module 11 and pacemaker/defibrillator 82 may also be used as a common electrode. The sharing of the lead 83 is made possible by the "Y" adaptor 99 that connects the lead 83 to both the electronics module 11 and pacemaker/defibrillator 82. It is also envisioned that either the "Y" adaptor 87 or the cardiosaver electronics module 11 might have surge protection circuitry to protect the cardiosaver during electrical stimulation discharges from the pacemaker/defibrillator 82. This is most important when the unit 82 is a defibrillator.

FIG. 8 illustrates a cardiosaver system 80 consisting of a internal equipment 81 and external equipment 307. The external equipment 307 includes a portable alarm system 260, a base/recharger 265, a physician's programmer 68 with antenna 70 for communicating with the internal equipment 81, and a programmer 75 with antenna 76 for communicating with the implanted pacemaker/defibrillator 82. Wireless signals 91 and 92 to and from the pacemaker/defibrillator programmer 75 from and to the implanted pacemaker/defibrillator 82 are used to program and collect data back from the pacemaker/defibrillator programmer 75 by the patient's physician.

The cardiosaver system 80 of FIG. 8 also shows the external alarm system 60 being a portable alarm system 260 that the patient can take with him when he is away from his primary location. For patient's confined to a fixed location like a nursing home or residence, the fixed location alarm system 160 of FIGS. 1, 6, and 7 may be adequate, but for patient's who are mobile, the portable alarm system 260 would be advantageous. A patient could certainly have both a fixed and portable alarm systems. It is envisioned that in many cases the portable alarm system 260 would be the only external alarm system 60 needed and a base/recharger 265 might be located by the patient's bedside for nightly recharging of the battery 266 of the portable alarm system 260. It should be understood that the cardiosaver 81 represents any of the following: a cardiosaver device; a cardiosaver that includes a separate drug port 78 as shown in FIG. 7 or a cardiosaver with an integrated drug port 128 as shown in FIGS. 10 through 13. Although the cardiosaver electronics module 11 and pacemaker/defibrillator 82 share the lead 83, it is also conceived that they could each have separate leads.

The portable alarm system 260 can be made small enough to be readily carried by the patient on a belt or in a pocket or purse. The portable alarm system 260 might look very much like an existing Internet ready cell phone. One button on the face of the portable alarm system 260 might be labeled or have an icon identifying the button as a panic button 252 whose function is described with respect to the panic button 52 of FIG. 1. The portable alarm system 260 would include a patient operated initiator 255, alarm speaker 257, cardiosaver communication antenna 261 and alarm transceiver 256 similar in function to those elements of the fixed location alarm system 160 of FIG. 1.

The purpose of the alarm transceiver 256 is to receive over the antenna 261 wireless signals 53 from the cardiosaver electronics module 11 indicating the detection of a cardiac event and to warn the patient by an audio signal 258 sent to the alarm speaker 257. The audio signal 258 could be a sequence of tones and/or a speech message that instructs the patient as to actions to be taken. Furthermore, the alarm transceiver 256 could then, depending upon the nature of the wireless signal 53, place an outgoing call or send a data message using the cell phone circuitry 88. The call or data message would be sent over the wireless link 95 that arrives at the network operation support system 110 of FIG. 6, which is located at a central network operation center. The network operation support system computer 130 (shown in FIG. 6) will then cause the incoming alarm message to be displayed on the diagnostic terminal 132 (shown in FIG. 6) of a medical professional. The medical professional would then call the patient back to the cell phone 88 built into the portable alarm system 260 to better ascertain the patient's condition and to let the patient know that emergency medical services are on their way or to provide other medical advice. A Global Positioning Satellite (GPS) receiver is now being built into many cell phones.

Such a GPS receiver 87 with antenna 97 could receive position information 93 from GPS satellites and this information could be passed on in data messages sent by the portable alarm system 260 to the network operation support system 110 of FIG. 6. Such GPS location information (or other means to determine the location of a cell phone) would allow emergency medical services to get to the patient anywhere that the cell phone circuitry 88 has sufficient signal from the cellular network to function. Today most digital cell phones include both paging and wireless Internet access. This capability can be utilized for the needed data messaging for the portable alarm system 260.

It is also envisioned that instead of a GPS receiver 87, a cellular network based patient locator could be used to identify the patient's position for forwarding to the emergency medical services.

Two or more of the antennas 261, 97 and 98 may be physically the same structure. It is envisioned that the entire circuitry of the portable alarm system 260 can be contained within the patient's cell phone. This has the added advantage to the patient of being able to use the portable alarm system for normal telephony. The cell phone circuitry 88 in FIG. 8 is that of a typical cell phone in that it can receive a wireless signal 94 into its antenna 98 or transmit a wireless signal 95 from its antenna 98.

Figure 9:
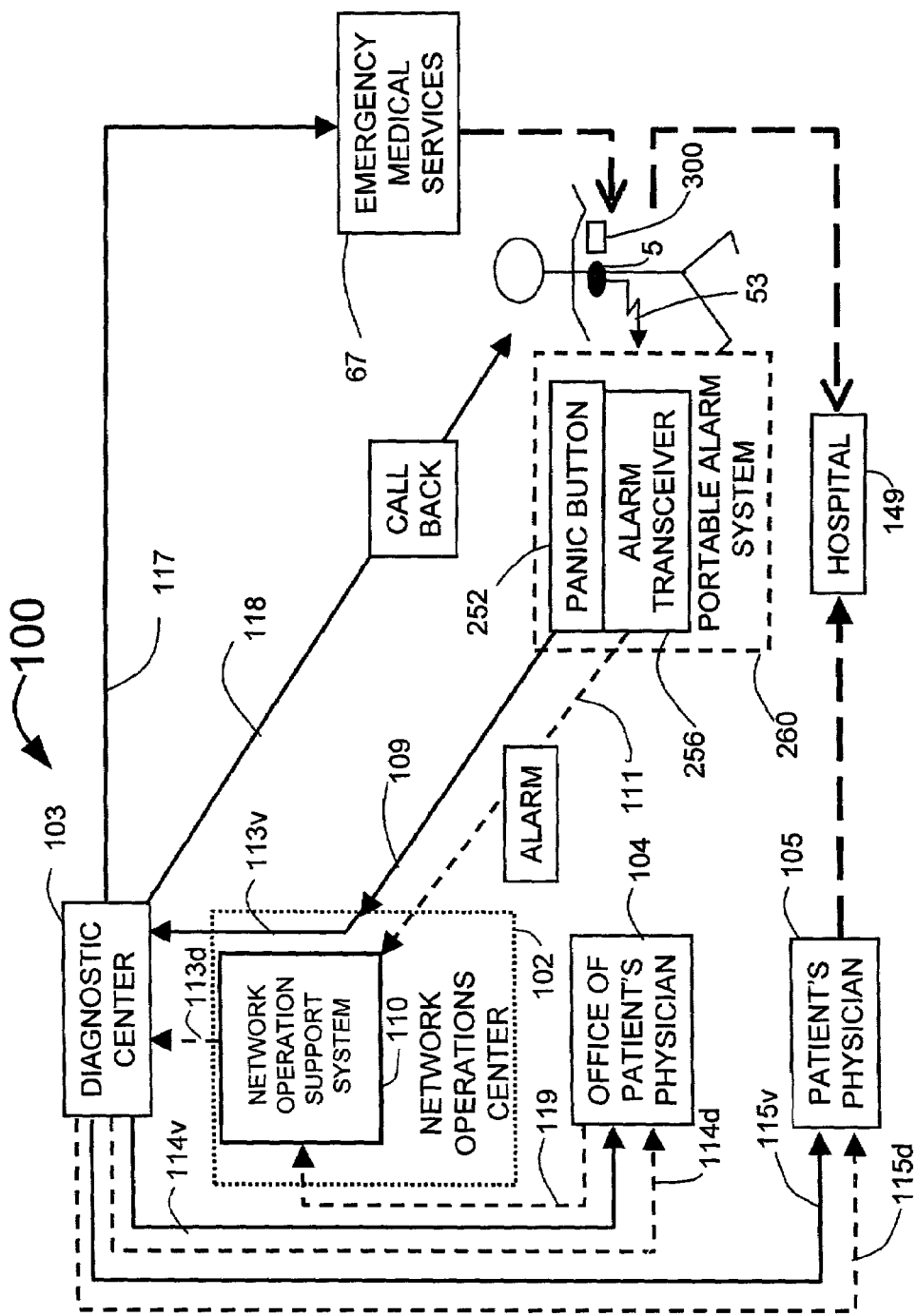
FIG. 9 is a block diagram of the cardiosaver system that illustrates the flow of data to and from a patient having a cardiac event.

FIG. 9 is a block diagram of a rapid treatment system 100 whose objective is to provide optimum treatment for a patient having a cardiac event such as heart attack, arrhythmia or a stroke. The optimum treatment involves administering to the patient a medication treatment as pre-prescribed by the patient's own doctor in case he has such a cardiac event. The administration of the medication should be accomplished as quickly as possible with the optimum treatment delay being less than 15 minutes and with an extremely high probability of providing the medication within 30 minutes. Furthermore, the optimum treatment can involve the intravenous injection of either or both a thrombolytic agent or an anti-thrombogenic medication and the application of mechanical vibration in the vicinity of the heart or brain to enhance the breaking up of an artery blocking blood clot. In the case of the detection of an arrhythmia, the medication that is to be delivered would be an anti-arrhythmia medication.

FIG. 9 shows a rapid treatment system 100 for an implanted cardiosaver 5 with portable alarm system 260. The rapid treatment system 100 would operate as follows:

1. When a cardiac event is detected by the cardiosaver 5, the cardiosaver sends an alarm detected message over the wireless signal 53 to the alarm transceiver 256 of the portable alarm system 260. The wireless signal 53 includes an input alarm signal into the alarm transceiver 256 as well as stored and real time electrogram data from the implanted cardiosaver 5.
2. The alarm transceiver sends an alarm message 111 to the network operation support system 110 located in the network operation center 102. The alarm message 111 includes an output alarm signal from the alarm transceiver 256 as well as stored and real time electrogram data from the implanted cardiosaver 5.
3. The network operation support system 110 in the network operation center 102 then identifies the next available medical practitioner at the diagnostic center 103 and transmits data 113$d$ that is displayed on the screen of the medical practitioner at the diagnostic center 103. The data 113$d$ includes the information received from the alarm transceiver 256 (e.g. alarm type and electrogram data), the phone number(s) of emergency medical services nearest to the patient's location as well as the relevant patient medical records and prescribed treatments stored in the database of the network operation support system 110 as described with the assistance of FIG. 6. Directions to the patient's location could be included as well as baseline electrogram data from earlier recordings taken at the office of the patient's personal physician.
4. The medical practitioner at the diagnostic center 103 can then call the patient back with a voice call 118 to ascertain the patient's status and to give instructions and assurances that his alarm has been received. This concept for closing the loop with the patient is analogous to the use of burglar alarm systems in a home that are triggered by the opening of a door when the alarm system is enabled. In that case, there is also an alarm message by telephone sent to some monitoring center and a return telephone call from the center to a person in the house.
5. The medical practitioner at the diagnostic center 103 could then call the emergency medical services 67 nearest the location of the patient to order an ambulance and, if so prescribed, the medications for the paramedics to administer upon arrival at the patient's location.
6. The medical practitioner at the diagnostic center 103 could then have a voice message 114$v$ and/or 115$v$ to the patient's physician 105 to inform that physician of his patient's status. If the patient's physician 105 is available either at his office 104 or by other means having remote data receiving capability, the electrogram data can also be sent by data message 114$d$ or 115$d$ for the physician's review.
7. If the patient is near his primary location, the physician 105 or an on-call doctor for the practice would be informed of the hospital 149 to which the ambulance of the emergency medical services 67 will be taking the patient. The physician 105 can then meet his patient at the hospital 149 if he elects to do so.

The transmission of these data can be originated either automatically in the event that a cardiac event occurs (e.g., a heart attack) for which the system is programmed to be activated in case of such an event, or the patient can be provided with a panic button 252 to make a direct phone call 109 into the diagnostic center 103. The phone call 109 would be routed through the network operation center 102 so that as the routed call 113$v$ is received by a medical practitioner, the appropriate patient record over data line 113$d$ is automatically displayed on the screen of the medical practitioner at the diagnostic center 103.

Such call routing and simultaneous data display is well known in the field of automatic call distribution systems provided by PBX or Centrex manufacturers and designed to work with Automatic Number Identification (ANI) sent through the public telephone network.

The patient would also be able to use the panic button line 109 to obtain a consultation from the medical practitioner at the diagnostic center 103 if he senses that there is something wrong with his heart and no alarm has been triggered. For example, if the patient is experiencing PVC's or PAC's, which are both fairly common and benign afflictions, he could trigger the panic button 252 for a review of his electrogram by a trained medical practitioner at the diagnostic center 103. The medical practitioner would then communicate with the patient over the line 118 as to what the analysis of his situation reveals. This capability could also be used if the patient experiences a stroke or other health related event where it is necessary to summon the emergency medical services 67.

When summoned, the diagnostic center 103 would provide to the emergency medical services 67 a sub-set of the data that the medical practitioner at the diagnostic center 103 has received. These data would include any or all of the following: (1) the patient's name; (2) the patient's location; (3) directions to the patient's location; (4) an analysis of the patient's condition; and (5) directions and the authority for administering medication(s) to the patient. If the panic button 252 is activated, the medical practitioner at the diagnostic center 103 would also call by the voice line 114$v$ to the office of the patient's physician 104. If the patient's physician was not available at his office, the diagnostic center 103 could use the voice message 115$v$ to directly call the patient's physician 105. In the event of an emergency medical condition of the patient, it is expected that the emergency medical services 67 would have its ambulance bring the patient to the hospital 149. The patient's physician 105 would also be informed so that he could assume the care of his patient at the hospital 149. It is also conceived that the patient would inform the diagnostic center 103 that he or his caretaker is taking him directly to the hospital and that emergency medical services are not necessary.

Although most of the voice and data communication described for the rapid treatment system 100 would be by ground telephone or fiber optic lines or by use of the ground-based cellular network(s), the use of orbiting communication satellites is clearly possible. If a person was traveling to a country where there was no cellular network, he could use a cell phone that utilizes satellite communication to enter the rapid treatment system 100 in order to gain advice about a cardiac event. For example, an American traveling through Africa could use a cell phone designed for satellite communication to enter the system 100. He could also carry appropriate drugs with him for self-treatment or treatment by a caretaker should a heart attack occur.

One other feature of the present invention shown in FIG. 9 is a mechanical vibrator 300 that can be applied to the patient's chest over his heart after heart attack medication has been injected into the patient's bloodstream. The application of ultrasonic or other types of vibration can provide a more rapid breakup of a blood clot in a coronary artery, thus providing more rapid perfusion of the patient's myocardium. It is also envisioned that such a vibrator 300 could be applied to the patient's head if medication is delivered to treat a stroke.

Figure 10:
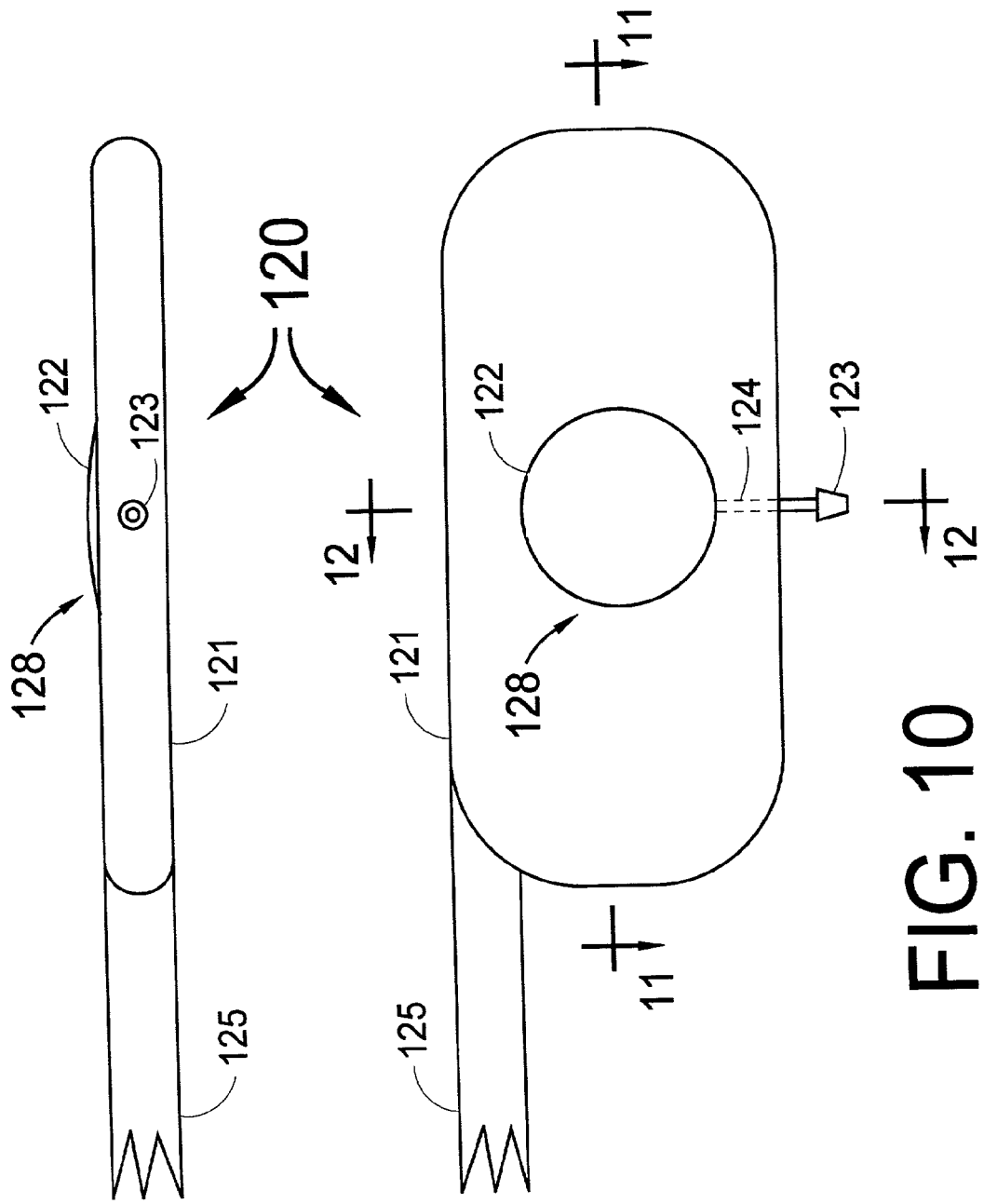
FIG. 10 is a plan view and a side view of a cardiosaver device that includes an integrated drug port.

FIG. 10 shows a top view and a plan view of a cardiosaver device 120 that includes an integrated pass-through drug port 128 that is capable of rapidly delivering a medication into the patient's bloodstream. It should be understood that the intravascular drug delivering cardiosaver 120 could include the capability of a pacemaker and/or a defibrillator. The cardiosaver 120 has a case 121, a septum 122 and an exit port 123 connected to an exit tube 124. An endovascular or subcutaneous lead 125 would be connected to the cardiosaver 120 in a manner as is well known in the art of pacemakers. The lead 125 could have as few as one or as many as eight electrodes that feed into the electronics module 127 (of FIG. 11). The lead can also include a drug passageway for delivering medication into the patient's bloodstream. The drug passageway could include a check valve near its distal end to prevent the inflow of blood into that drug delivery passageway. The case 121 could also act as an indifferent electrode for the cardiosaver 120.

FIG. 11 is a cross section of the cardiosaver 120 at section 11—11 of FIG. 10. FIG. 11 shows a drug chamber 130, a battery 126 and an electronics module 127 all contained within the cardiosaver 120. FIG. 12 is a cross section of cardiosaver 120 at section 12—12 of FIG. 10. Shown in both FIGS. 11 and 12 is the septum 122 that is the outermost part of the drug port 128 that is shown in greater detail in FIG. 13. Also shown in FIGS. 11 and 12 is a FIG. 13 shows a highly enlarged cross section of the drug port 128 of the cardiosaver 120 that has a case 121 to which an electrical insulating disc 136 is attached. Both FIGS. 12 and 13 show the cross section of the electrical lead 125 and the electrical insulating disk 136 that separates the conducting surface 137 from the metal case 121 of the cardiosaver 120. In FIG. 12, the contact points 134 attached to the bottom plate 133 of the bellows 132 do not make contact with the top surface of the conducting surface 137. As seen in FIG. 13, when the point of a non-coring needle 140 attached to a hypodermic syringe (not shown) is pushed downward against the bottom plate 133 of the metal bellows 132, at least one of the contact points 134 will close an electrical circuit that will cause a unique audio signal to be generated by the circuitry within the electronics module 127 of the cardiosaver 120. This signal will inform the patient, caretaker, paramedic or medical professional who has placed the needle through the patient's skin that he can now push down on the plunger of the hypodermic syringe to deliver medication through the medication delivery catheter 152 directly into the patient's bloodstream. When the medication is delivered in this manner through the opening 141 in the needle 140, the type and quantity of drug(s) as prescribed by the patient's physician will be rapidly injected into the patient's bloodstream. The medication will flow from opening 141 through the drug chamber 130, out the exit tube 124, through the exit port 123 and finally out of the medication delivery catheter 152 having a check valve 153 located near its distal end. The unique audio signal indicating that the needle 140 is in its proper place in the drug chamber 138 can be a continuous sound or a rapid succession of audio pulses or any other audio signal that is distinctly different from the alarm audio signals that are related to the detection of a cardiac event.

An important advantage in the use of the cardiosaver 120 is that the patient or the patient's caretaker can keep on hand the amount and type of medication(s) that the patient's doctor has prescribed for that patient. For example, an amount of tPA, urokinase, ReoPro or any other medication or blend of medications that would be used for rapid treatment in the event of an alarm signifying a heart attack (or a stroke) could be kept where the patient and/or his caretaker could readily get it. The medication may be stored in a refrigerator, possibly already within a hypodermic syringe. The medication could also be kept in the form of a powder and mixed with a solvent at the time when it was required for injection. A travel pack that includes the prescribed medication and a means for its delivery through the drug port 128 of the cardiosaver 120 could also be provided for when the patient is away from his home. The patient or his caretaker could also have a source of mechanical vibration to apply to the patient's chest over his heart to enhance the action of the delivered medication in breaking up a blood clot that is blocking a coronary artery. The patient or his caretaker could also have on hand an external defibrillator to treat the patient if defibrillation is needed.

Although the needle 140 in FIG. 13 is shown being placed away from the center of the septum 122, a patient or his caretaker would try to place the needle through a tattoo mark 143 that is placed over the center of the septum after the cardiosaver 120 is implanted. The shape of the tattoo mark on the patient's skin could be a dot, a small circle, a crosshairs or any other shape that clearly marks the location of the center of the septum 122. The color of the tattoo should be different from normal marks found on the patient's skin. The location of the septum 122 could also be discerned by feeling it directly under the patient's skin.

FIGS. 14 and 15 show details of a distal portion of the medication delivery catheter 150 through which medication is to be delivered into the patient's bloodstream. The medication delivery catheter 150 is essentially a cylindrical tube 152 that is closed at its distal end and has a check valve 155 located just proximal from its distal end. When no medication is being delivered through the medication delivery catheter 150, the check valve 155 has a closed slit 154A as shown in FIGS. 14 and 15A. When a bolus of medication is being delivered by means of a drug delivery device (such as a hypodermic syringe) through the cardiosaver 120, (or through a separate drug port or a drug port used with a pacemaker or defibrillator) the elastomer sheath 153 will open to allow the medication to flow through the open slit 154B and into the patient's bloodstream. By this means and method, a patient having an acute myocardial infarction can be rapidly treated to prevent damage to his heart muscle. Also, anti-arrhythmic medication could be delivered in this manner if the cardiac event detected by the cardiosaver 120 is a potentially dangerous arrhythmia.

The medication delivery catheter 150 would optimally be a non-kinking type of plastic tube that is well known in the art of implanted catheters. The elastomer sheath 153 might advantageously be formed from silicone rubber that could be shrink fit over the closed slit 154A. After the cardiosaver 150 is implanted like a pacemaker beneath the patient's skin, the drug port can be accessed at regular intervals (e.g., once a year) by the patient, his caretaker or his physician to push through an anti-bacterial, sterile solution to verify that the access port is still viable. This procedure would also serve as a training exercise for the patient or his caretaker by causing the needle-in-place audio signal to be created so that that function of the cardiosaver 120 can be verified.

Figure 16:
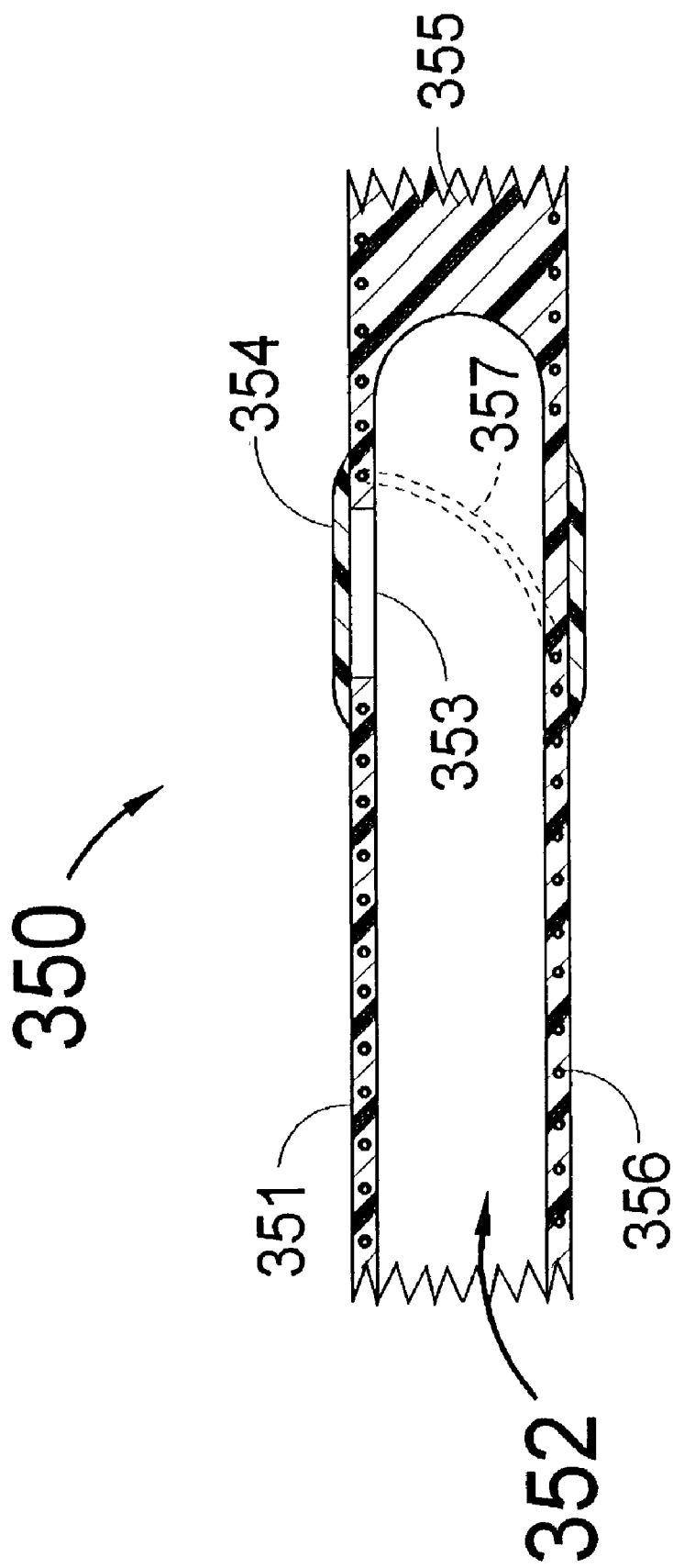
FIG. 16 is a longitudinal cross section of a cardiosaver combined electrical lead that includes a drug delivery lumen and check valve.

FIG. 16 shows the longitudinal cross section of a catheter-lead 350 that is a combined electrical lead and medication delivery catheter. It is clearly envisioned to be able to combine the lead 125 of FIG. 13 with the medication delivery catheter 150 of FIGS. 14 and 15. FIG. 16 shows a hollow tube 351 that encloses a drug lumen 352 that terminates in a slit 353 covered by an elastomer sheath 354. The operation of this medication delivery catheter portion of the catheter-lead 350 would be the same as described for the medication delivery catheter 150 of FIGS. 14 and 15. The solid elastomer end section 355 of the catheter-lead 350 would prevent the drug from passing through the entire length of the catheter-lead 350. Also shown in FIG. 16 is a helical coil wire 356 that has an electrical connecting section 357 at that place along the catheter-lead 350 where the slit 353 is located. It should be understood that, although side slits are shown in FIGS. 14–16, the check valve could also be located at the distal end of either the medication delivery catheter 150 or the combined catheter-lead 350.

It is envisioned that the cardiosaver systems described herein would be of particular value to diabetic patients who are well known to have an acute myocardial infarction without any discernible symptoms. A method for helping such patients would be as follows:

(a) test the patient to determine if his fasting blood sugar exceeds 110 mg/dl, thereby indicating that he is a diabetic;

(b) determine if the patient is a likely candidate for an acute myocardial infarction because he has had either one, several or all of the following coronary problems: hypercholesterolemia, high blood pressure, a prior stroke, a prior heart attack; proteinuria with a level exceeding 250 mg in a 24 hour period, atherosclerotic disease within his coronary arteries, bypass surgery or a family history of heart attacks, a homocysteine level greater than 9 mcmol/L, a c-reactive protein level greater than 1.1 mg/dl, an age over 65 years; and (c) implant a cardiosaver within the patient, the cardiosaver having the capability for determining that an acute myocardial infarction is occurring and warning the patient that he should seek emergency medical assistance.

Such a method when used for diabetic patients could significantly reduce morbidity and mortality associated with acute myocardial infarction. The method including just items (b) and (c) above would also be valuable for preventing death from a heart attack.

Although throughout this specification all patients have been referred to in the masculine gender, it is of course understood that patients could be male or female. Furthermore, although the only electrogram indication for an acute myocardial infarction that is discussed herein is a deviation of the ST segment, it should be understood that other changes in the electrogram (depending on where in the heart the occlusion has occurred and where the electrodes are placed) could also be used to determine that an acute myocardial infarction is occurring. Furthermore, sensors such as heart motion sensors, or devices to measure pressure, $pO_2$ or any other indication of an acute myocardial infarction could be used independently or in conjunction with a ST segment deviation detector to sense a cardiac event.

It is expected that patient's undergoing one or more symptoms of a stroke could use the cardiosaver system to have an anti-thrombogenic medication and/or a thrombolytic medication injected through an implanted drug port to reduce damage to the brain. Upon the occurrence of such symptom(s), the patient could contact a medical practitioner at the diagnostic center to verify if he (the patient) should have such a pre-prescribed medication injected. Such a system could use a screening procedure by which patients who are prone to a hemorrhagic stroke would not be allowed to utilize this system. Screening out potential patients who might have a hemorrhagic stroke includes determining if such patients have an aneurysm in a coronary artery or an arterio-venous malformation in the cerebral circulation. Patients who have had episodes of atrial fibrillation, transient ischemic attacks (TIAs), a prior heart attack or ischemic stroke could use the method described herein for heart attack patients that utilize a drug port and external network operation support system to gain medical assistance for the administration of a drug to decrease the morbidity and mortality associated with ischemic stroke.

Various other modifications, adaptations, and alternative designs are of course possible in light of the above teachings. Therefore, it should be understood at this time that, within the scope of the appended claims, the invention can be practiced otherwise than as specifically described herein. Furthermore, for the purposes of these claims, the word "including" shall have the same meaning as "comprising" and the word "designed" or "for" shall have the same meaning as "adapted".

What is claimed is:

1. An implanted medical device which is a cardiosaver device that is designed for rapid treatment of a heart attack of a human patient, the medical device including:

an implanted sensor for detecting the occurrence of the heart attack of the human patient;

an alarm that produces an alarm signal for indicating to the human patient that a heart attack is occurring when the sensor to which the alarm is electrically coupled detects the occurrence of a heart attack; and, a pass-through drug port implanted within the human patient, the drug port being designed to be used with an externally located drug delivery device for injecting medication into the bloodstream of the human patient at a time after the alarm indicates that a heart attack is occurring.

2. The cardiosaver device of claim 1 wherein the implantable sensor is two or more electrodes.

3. The cardiosaver device of claim 2 wherein one of the electrodes is a first electrode and the cardiosaver device include an electronics module that has a metal case that acts as a second electrode.

4. The cardiosaver device of claim 1 wherein the sensor has an output electrical signal which is the electrogram of the human patient and there is electronics circuitry contained within the electronics module, the electronics circuitry being designed to detect the occurrence of a heart attack from a change of the sensor's output electrical signal when compared to the sensor's output signal when no heart attack is occurring.

5. The cardiosaver device of claim 4 wherein the electronics circuitry within the electronics module includes a detector for detecting a variation of the ST segment of the electrogram as an indication of the heart attack.

6. The cardiosaver device of claim 4 wherein the electronics circuitry within the electronics module includes capability for recording an electrogram signal from the sensor, the recorded electrogram being retained in memory for playback at a later time.

7. The cardiosaver device of claim 1 wherein the alarm of the cardiosaver system includes a subcutaneous electrical tickle which is an electrical stimulation.

8. The cardiosaver device of claim 1 wherein the alarm includes an implanted audio device having an alarm output that can be sensed by the human patient.

9. The cardiosaver device of claim 1 further including an external alarm system that is situated externally from the human patient for indicating to the human patient that he is experiencing a heart attack.

10. The cardiosaver device of claim 1 further including a self-sealing septum, drug chamber and exit port each being a part of the drug port, and the drug delivery device being a hypodermic syringe that includes a needle having a sharp point at its distal end, the sharp point being designed to be placed through the self-sealing septum of the drug port.

11. The cardiosaver device of claim 10 further including a medication delivery catheter that is joined to the exit port, the medication delivery catheter having a distal portion that is placed into the patient's bloodstream.

12. The cardiosaver device of claim 11 further including a check valve located at the distal portion of the medication delivery catheter.

13. The cardiosaver device of claim 10 further including an electronics module that is part of the cardiosaver device and the pass-through drug port is structurally integrated into the electronics module.

14. The cardiosaver device of claim 13 wherein the externally located drug delivery device includes a drug delivery needle that is designed to pass through the self-sealing septum of the drug port, the cardiosaver device also having the capability to create an audio signal when the distal end of the needle is properly positioned for delivery of medication into and through the drug port and into the human patient's bloodstream.

15. The cardiosaver device of claim 14 wherein the audio signal indicating that the needle is properly positioned is a unique audio signal that is different from the audio alarm signal that indicates that a heart attack is occurrnng.

16. The cardiosaver device of claim 1 further including an electronics module that is part of the cardiosaver device and the drug port is structurally separated from the electronics module.

17. The cardiosaver device of claim 1 wherein the alarm signal indicating that a heart attack is occurring has a first alarm pattern, the first alarm pattern being a different pattern as compared to a second pattern of alarm signal that indicates that there is insufficient blood flow in at least one coronary artery of the human patient as a result of increased work load of the heart due to exercise.

18. The cardiosaver device of claim 1 further including the electronic circuitry of a heart pacemaker for electrically pacing the heart of the human patient.

19. The cardiosaver device of claim 1 further including electronic circuitry for an implantable cardiac defibrillator designed to electrically shock the heart of the human patient if ventricular fibrillation is detected.

20. The cardiosaver device of claim 1 further including an implanted electronics module designed to be implanted within the human patient, the electronics module having a wireless transmitter that can communicate by a wireless signal with an externally located receiving system thus providing a wireless communication system.

21. In combination, an implanted medical device and external equipment, the combination being a cardiosaver system designed for the rapid treatment of a heart attack of a human patient, the system including:

an implanted medical device that includes an implanted electronics module and at least one sensor that is electrically coupled to the sensor, the medical device being designed for detecting the occurrence of the heart attack of the human patient;

an alarm that produces an alarm signal for indicating to the human patient that a heart attack is occurring when the sensor to which the alarm is electrically coupled detects the occurrence of a heart attack;

a pass-through drug port implanted within the human patient, the drug port being designed to cooperate with an externally located drug delivery device for injecting medication into the bloodstream of the human patient at a time after the alarm indicates to the human patient that a heart attack is occurring; and external equipment having the capability to send wireless signals to and receive wireless signals from the implanted electronics module.

22. The cardiosaver system of claim 21 wherein the external equipment includes an external alarm system that is designed to indicate to the human patient that a heart attack is occurring.

23. The cardiosaver system of claim 22 wherein the external alarm system is a fixed location alarm system located at the place where the human patient normally resides.

24. The cardiosaver system of claim 22 wherein the external alarm system is a portable alarm system that is designed to be carried by the human patient.

25. The cardiosaver system of claim 21 wherein the external equipment includes an external alarm system that is designed to inform the human patient that a heart attack has been detected, the external equipment also including a rapid treatment system that is coupled to the external alarm system, the rapid treatment system being designed to provide medical assistance from a medical practitioner for the human patient when the external alarm system indicates that a heart attack has occurred, the medical practitioner being located at a site that is remote from the human patient.

26. The cardiosaver system of claim 25 wherein the external equipment is designed to provide medical advice to the human patient, the medical advice originating from at least one of the two systems that include the external alarm system and the rapid treatment system.

27. The cardiosaver system of claim 26 wherein the medical advice includes a description of at least one medication that is to be taken by the human patient.

28. The cardiosaver system of claim 26 wherein the medical advice includes instructions to proceed immediately to an emergency medical facility.

29. The cardiosaver system of claim 26 wherein the medical advice includes the statement that an ambulance from emergency medical services is on its way to bring the patient to an emergency medical facility.

30. The cardiosaver system of claim 26 wherein the medical advice is a collection of verbal directions to get a pre-prescribed medication that is located within the place where the human patient resides and to use a hypodermic syringe to deliver that medication through the drug port of the implanted cardiosaver device and into the bloodstream of the human patient.

31. The cardiosaver system of claim 21 wherein the external equipment includes an external alarm system that is designed to call a medical practitioner at a diagnostic center by means of a telephone link.

32. The cardiosaver system of claim 21 wherein the electronics module is designed to store electrogram data in stored electrogram circuitry and to send these data to the external equipment by means of the wireless signal from the implanted electronics module.

33. The cardiosaver system of claim 32 wherein the external equipment is designed to send to a diagnostic center a collection of data that includes, but is not limited to, at least one of the following, the patient's real time electrogram, the patient's stored electrogram, the patient's heart rate and the patient's identification number, any of these data being sent to the external equipment by means of the wireless signal from the implanted electronics module.

34. The cardiosaver system of claim 21 wherein the external equipment includes a portable alarm system that is designed to be carried by the human patient, the portable alarm system being designed to receive the wireless signal from the implanted electronics module and to inform the human patient of the occurrence of a heart attack by means of an audio signal.

35. The cardios aver system of claim 21 wherein the external equipment includes a fixed location alarm system that is designed to be situated at the place where the human patient normally resides, the fixed location alarm system being designed to receive the wireless signal from the implanted electronics module and to inform the human patient of the occurrence of a heart attack by means of an audio signal.

36. The cardiosaver system of claim 21 wherein the external equipment includes a physician's programmer located externally from the human patient, the physician's programmer being designed to send wireless signals to and receive wireless signals from the implanted electronics module.

37. The cardiosaver system of claim 36 wherein the implanted medical device includes the capability for sensing, recording and transmitting by the wireless signal to the physician's programmer, the data being selected from at least one of the group that includes: the real time electrogram, the stored electrogram, the heart rate and the patient's unique identification number, the physician's programmer being designed to store and display the data that is transmitted.

38. The cardiosaver system of claim 37 wherein the physician's programmer is designed to visually display the data received from the implanted electronics module.

39. The cardiosaver system of claim 36 wherein the physician's programmer is in the form of a laptop computer that is designed to send a wireless signal for programming the implanted medical device, the wireless signal being received by the implanted electronics module of the implanted medical device.

40. The cardiosaver system of claim 36 wherein the implanted electronics module is designed to receive command programming instructions from the externally located physician's programmer.

41. The cardiosaver system of claim 36 wherein the implanted electronics module includes an audio alarm that produces a sound to inform the human patient when a heart attack is detected, the physician's programmer being designed to program the implanted electronics module to adjust the intensity of the sound from the audio alarm.

42. The cardiosaver system of claim 36 wherein the implanted electronics module includes a subcutaneous electrical tickle device that produces an electrical stimulation signal to inform the human patient when a heart attack is detected, the physician's programmer being designed to adjust the intensity of the electrical stimulation signal.

43. The cardiosaver system of claim 36 wherein the implanted electronics module can be programmed by the physician's programmer to a specific threshold voltage for the ST segment of the electrogram so that, for any voltage detected having a greater magnitude as compared to that specific threshold voltage, the electronics module would indicate that a heart attack has been detected.

44. The cardiosaver system of claim 21 further including implanted heart pacemaker electronic circuitry for electrically pacing the heart of the human patient.

45. The cardiosaver system of claim 44 wherein the implanted electronics module includes the heart pacemaker electronic circuitry within a single case.

46. The cardiosaver system of claim 44 wherein the heart pacemaker electronic circuitry is contained within a first case and electronic circuitry for the detection of a heart attack is contained within a second case that is separate from the first case.

47. The cardiosaver system of claim 21 further including implanted defibrillator electronic circuitry designed to electrically shock the heart of the human patient if ventricular fibrillation is detected.

48. The cardiosaver system of claim 47 wherein the implanted defibrillator electronics circuitry and circuitry for the detection of a heart attack are both contained within a single case.

49. The cardiosaver system of claim 47 wherein the defibrillator electronic circuitry is contained within a first case and electronic circuitry for the detection of a heart attack is contained within a second case that is separate from the first case.

50. The cardiosaver system of claim 21 wherein the implanted electronics module includes an audio alarm.

51. The cardiosaver system of claim 21 wherein the implanted electronics module includes a vibration device, the vibration device being designed to indicate to the human patient that a heart attack is occurring by means of the human patient sensing the vibration.

52. The cardiosaver system of claim 21 wherein the external equipment includes a medication for injection through the drug port into the bloodstream of the human patient.

53. The cardiosaver system of claim 52 wherein the medication for injection through the drug port is selected from the group that includes a thrombolytic medication, an anti-thrombogenic medication or a combination of thrombolytic and anti-thrombogenic medications.

54. The cardiosaver system of claim 53 wherein the thrombolytic medication and anti-thrombogenic medication are selected from at least one of the group that includes tPA, urokinase, streptokinase, ReoPro, heparin, Plavix and any pharmaceutical analog of any one of these medications.

55. The cardiosaver system of claim 52 further including a means for applying vibration into the region of the heart of the human patient at a time after a medication has been injected into the bloodstream of the human patient, the vibration being applied for the purpose of enhancing the rapid break up of any blood clot formed in a coronary artery of the human patient.

56. The cardiosaver system of claim 55 wherein the vibration is applied by means of a device that generates an ultrasonic vibration.

57. The cardiosaver system of claim 21 wherein the externally located drug delivery device is a hypodermic syringe.

58. The cardiosaver system of claim 57 wherein the hypodermic syringe has a needle that has an opening for delivering medication into the drug port and the implanted cardiosaver is designed to produce an audio signal when the opening is properly positioned for delivering the medication into the drug port.

59. The cardiosaver system of claim 58 wherein the audio signal when the needle opening is properly positioned within the drug port is distinctly different from the audio alarm signal that indicates that a heart attack is occurring.

60. An implanted cardiosaver device designed to detect both serious and non-emergency cardiac events of a human patient, the device including:
an electronic module that includes electronic circuitry for detecting the occurrence of at least two different types of cardiac events, at least one of those two events being a serious event so that immediate emergency action is required and the other cardiac event being a non-emergency event that is not serious so that no emergency action is required; and,
an alarm for informing the human patient that either a serious or a non-emergency cardiac event is occurring, the alarm having two different alarm signals, a first type of alarm signal for a serious event and a second and different type of alarm signal for a non-emergency event that is not serious.

61. The cardiosaver device of claim 60 wherein the second type of alarm signal is triggered by ischemia of a coronary artery that is a result of increased effort by the patient, which cardiac event is a non-emergency event that is not serious.

62. The cardiosaver device of claim 60 wherein one of the cardiac events that can trigger either a first type of alarm signal or a second type of alarm signal is a heart arrhythmia, the selection of the first type or second type of alarm signal being dependent upon whether or not the arrhythmia is life threatening.

63. The cardiosaver device of claim 62 wherein the cardiosaver can detect at least one type of arrhythmia that is selected from the group that includes bradycardia, tachycardia, atrial fibrillation, atrial flutter, ventricular fibrillation, premature ventricular contractions (PVCs) and premature atrial contractions (PACs).

64. The cardiosaver device of claim 60 wherein the first type of alarm signal is generated by the cardiosaver device when a heart attack occurs.

65. The cardiosaver device of claim 60 further comprising a pass-through drug port implanted within the human patient, the drug port including a self-sealing septum through which a bolus of medication to treat the cardiac event can be rapidly injected into the bloodstream of the human patient using an externally located drug delivery device that is situated outside the body of the human patient.

66. The cardiosaver device of claim 65 wherein the externally located drug delivery device is a hypodermic syringe having a sharp end point for penetrating the septum of the drug port, the cardiosaver having the capability to produce a unique audio signal when the end point is pushed against a bottom plate of the drug port.

67. The cardiosaver device of claim 60 wherein the electronics module that is part of the cardiosaver device includes a digital memory for storing electrograms of the human patient.

68. In combination an implanted medical device and external equipment, the combination being a cardiosaver system, the cardiosaver system being designed to provide rapid treatment of a cardiac event of a human patient, the cardiosaver system including:
an implanted cardiosaver device which includes a sensor and electronics module for detecting the occurrence of a cardiac event and an alarm for informing the human patient that a cardiac event is occurring, the implanted cardiosaver device being designed to include wireless communication means capable of transmitting an input alarm signal from the implanted cardiosaver device to an alarm transceiver that is located outside of the body of the human patient;
an external alarm system including the alarm transceiver and an audio alarm speaker, the alarm transceiver being designed to receive the input alarm signal from the implanted cardiosaver device and transmit an output alarm signal and a data signal to a remote location indicating that a cardiac event has occurred; and
a network operation support system for receiving the output alarm signal and the data signal from the alarm transceiver of the external alarm system and, upon receipt of the output alarm signal, indicate to a medical practitioner that an alarm has occurred indicating that the human patient has had a cardiac event.

69. The cardiosaver system of claim 68 wherein the cardiac event is a heart attack.

70. The cardiosaver system of claim 68 wherein the cardiac event is a heart arrhythmia.

71. The cardiosaver system of claim 70 wherein the cardiosaver device can detect at least one type of arrhythmia selected from the group that includes bradycardia, tachycardia, atrial fibrillation, atrial flutter, ventricular fibrillation, premature ventricular contractions (PVCs) and premature atrial contractions (PACs).

72. The cardiosaver system of claim 68 wherein the cardiac event is ischemia of the myocardium resulting from the human patient undergoing increased physical activity.

73. The cardiosaver system of claim 68 wherein the input alarm signal is designed to produce different alarm indications for different types of cardiac events detected by the implanted cardiosaver.

74. The cardiosaver system of claim 68 further including a pass-through drug port implanted within the human patient, the drug port including a self-sealing septum through which medication to treat the cardiac event can be rapidly injected into the bloodstream of the human patient using an externally located drug delivery device that is situated outside the body of the human patient.

75. The cardiosaver system of claim 68 further including electrogram storage circuitry within the electronics module of the implanted cardiosaver device, the electrogram storage circuitry being designed to store an electrogram provided by the sensor, the implanted cardiosaver device being designed to transmit the stored electrogram to the external alarm system and the external alarm system being designed to transmit the stored electrogram to the network operation support system for analysis by a medical practitioner situated at a diagnostic center.

76. The cardiosaver system of claim 75 wherein the stored electrogram includes a time period prior to the detection of the cardiac event.

77. The cardiosaver system of claim 75 wherein the stored electrogram includes a time period after detection of the cardiac event.

78. The cardiosaver system of claim 75 wherein the network operation support system is further designed to transmit the stored electrogram and the output alarm signal to a medical practitioner who is the personal physician of the human patient.

79. The cardiosaver system of claim 75 wherein the network operation support system is further designed to transmit the stored electrogram data to emergency medical services.

80. The cardiosaver system of claim 75 wherein the network operation support system includes a patient's record data base, the data base including data for a specific human patient who has a specific personal physician, the data base including a medication prescription for treatment of the human patient in the event of a heart attack, the medication prescription having been stipulated by the human patient's personal physician.

81. The cardiosaver system of claim 80 wherein the network operation support system is designed to transmit the medication prescription for treatment of the specific human patient to the emergency medical services, the medication prescription having been stipulated by a medical practitioner at the diagnostic center.

82. The cardiosaver system of claim 68 wherein the network operation support system includes a patient record database.

83. The cardiosaver system of claim 68 wherein the external alarm system is portable and is designed to transmit the data signal by means of a wireless telephone network.

84. The cardiosaver system of claim 68 wherein the external alarm system further includes means for locating the position of the human patient.

85. The cardiosaver system of claim 84 wherein the means for locating the position of the human patient is achieved by the use of the global positioning satellite system.

86. The cardiosaver system of claim 68 wherein the output alarm signal from the alarm transceiver is directed through an orbiting satellite to the network operation support system.

87. An implanted medical device to be used for the rapid treatment of a heart attack of a human patient, the medical device including the following parts:

at least one electrode placed into the heart of the human patient, the electrode being placed so that it produces an electrical signal that indicates when a heart attack is occurring;

an alarm system electrically coupled to the electrode, the alarm system being designed to inform the human patient that a heart attack is occurring when the electrical signal from the at least one electrode indicates that a heart attack is occurring; and, a pass-through drug port implanted within the human patient, the drug port being designed to be used with a hypodermic syringe for injecting medication through the drug port and into the bloodstream of the human patient after the alarm system indicates that a heart attack is occurring.

88. The implanted medical device of claim 87, where the medication injected into the bloodstream of the human patient is designed to dissolve a blood clot in a coronary artery of the human patient.

* * * * *